United States Patent
Gopalsami et al.

(10) Patent No.: US 8,165,682 B2
(45) Date of Patent: Apr. 24, 2012

(54) SURFACE ACOUSTIC WAVE PROBE IMPLANT FOR PREDICTING EPILEPTIC SEIZURES

(75) Inventors: Nachappa Gopalsami, Naperville, IL (US); Stanislav Kulikov, Sarov (RU); Ivan Osorio, Leawood, KS (US); Apostolos C. Raptis, Downers Grove, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 1013 days.

(21) Appl. No.: 11/496,195

(22) Filed: Jul. 31, 2006

(65) Prior Publication Data
US 2007/0073150 A1   Mar. 29, 2007

Related U.S. Application Data

(60) Provisional application No. 60/721,911, filed on Sep. 29, 2005.

(51) Int. Cl.
*A61N 1/00* (2006.01)
*A61B 5/04* (2006.01)
*A61B 5/05* (2006.01)

(52) U.S. Cl. ............. 607/45; 607/21; 607/32; 607/76; 600/378; 600/412

(58) Field of Classification Search .......... 607/21, 607/32, 45, 76; 600/378, 412; 60/21, 32, 60/45, 76
See application file for complete search history.

(56) References Cited

U.S. PATENT DOCUMENTS

| | | | | |
|---|---|---|---|---|
| 5,517,206 | A * | 5/1996 | Boone et al. | 343/806 |
| 5,914,692 | A * | 6/1999 | Bowers et al. | 343/742 |
| 5,995,868 | A | 11/1999 | Dorfmeister et al. | |
| 6,018,682 | A * | 1/2000 | Rise | 607/45 |
| 6,354,299 | B1 * | 3/2002 | Fischell et al. | 128/899 |
| 6,459,936 | B2 * | 10/2002 | Fischell et al. | 607/45 |
| 6,471,087 | B1 * | 10/2002 | Shusterman | 221/2 |
| 6,549,504 | B2 | 4/2003 | Osorio et al. | |
| 6,560,486 | B1 | 5/2003 | Osorio et al. | |
| 6,587,727 | B2 | 7/2003 | Osorio et al. | |
| 6,647,296 | B2 * | 11/2003 | Fischell et al. | 607/45 |
| 6,671,556 | B2 | 12/2003 | Osorio et al. | |
| 6,681,135 | B1 * | 1/2004 | Davis et al. | 607/21 |
| 6,731,976 | B2 * | 5/2004 | Penn et al. | 600/544 |
| 6,746,474 | B2 * | 6/2004 | Saadat | 607/105 |

(Continued)

FOREIGN PATENT DOCUMENTS

WO    WO 97/26823    7/1997

(Continued)

OTHER PUBLICATIONS

C. Campbell, "Surface Acoustic Wave Devices and Their Signal Processing Applications," Boston: Academic Press, 1989.

(Continued)

*Primary Examiner* — Nicole F Lavert
(74) *Attorney, Agent, or Firm* — Foley & Lardner LLP

(57) ABSTRACT

A system and method for predicting and avoiding a seizure in a patient. The system and method includes use of an implanted surface acoustic wave probe and coupled RF antenna to monitor temperature of the patient's brain, critical changes in the temperature characteristic of a precursor to the seizure. The system can activate an implanted cooling unit which can avoid or minimize a seizure in the patient.

15 Claims, 17 Drawing Sheets

U.S. PATENT DOCUMENTS

| | | |
|---|---|---|
| 6,768,969 B1 | 7/2004 | Nikitin et al. |
| 6,793,670 B2 | 9/2004 | Osorio et al. |
| 6,920,357 B2 | 7/2005 | Osorio et al. |
| 7,003,352 B1 * | 2/2006 | Whitehurst ............ 607/45 |
| 7,120,489 B2 * | 10/2006 | Shalev et al. ............ 607/2 |
| 7,209,787 B2 * | 4/2007 | DiLorenzo ............ 607/45 |
| 7,231,254 B2 * | 6/2007 | DiLorenzo ............ 607/45 |
| 7,366,571 B2 * | 4/2008 | Armstrong ............ 607/45 |
| 2002/0072776 A1 | 6/2002 | Osorio et al. |
| 2002/0072782 A1 | 6/2002 | Osorio et al. |
| 2002/0099412 A1 * | 7/2002 | Fischell et al. ............ 607/3 |
| 2003/0187621 A1 | 10/2003 | Nikitin et al. |
| 2003/0195574 A1 | 10/2003 | Osorio et al. |
| 2004/0082984 A1 | 4/2004 | Osorio et al. |
| 2004/0106967 A1 * | 6/2004 | Von Arx et al. ............ 607/60 |
| 2004/0138536 A1 | 7/2004 | Frei et al. |
| 2004/0138721 A1 | 7/2004 | Osorio et al. |
| 2006/0224216 A1 * | 10/2006 | Pless et al. ............ 607/62 |
| 2008/0021514 A1 * | 1/2008 | Pless ............ 607/45 |

FOREIGN PATENT DOCUMENTS

| | | |
|---|---|---|
| WO | WO 01/75660 | 10/2001 |
| WO | WO 03/046756 | 6/2003 |
| WO | WO 2004/032720 | 4/2004 |
| WO | WO 2004/034231 | 4/2004 |
| WO | WO 2004/034879 | 4/2004 |
| WO | WO 2004/034880 | 4/2004 |
| WO | WO 2004/034881 | 4/2004 |
| WO | WO 2004/034882 | 4/2004 |
| WO | WO 2004/034982 | 4/2004 |
| WO | WO 2004/036372 | 4/2004 |

OTHER PUBLICATIONS

S.H. Sheen, H. T. Chien, and A. C. Raptis, "Ultrasonic Techniques for Detecting Helium Leaks," pp. 1-13.

A. Pohl, "A Review of Wireless SAW Sensors," IEEE Transactions on Ultrasonics, Ferroelectrics and Frequency Control, vol. 47 No. 2, p. 317-332, Mar. 2000.

S.M. Kulikov, "The Saw Temperature Sensor Testing Technique," Technical Report; International Science and Technical Center (ISTC), the USA Energy Department and BIOFIL ltd., Apr. 30, 2004.

N. Gopalsami, et al., "SAW Microsensor Brain Implant for Prediction and Monitoring of Seizures," IEEE Sensors Journal, May 2006.

\* cited by examiner

SURFACE ACOUSTIC WAVE PROBE IMPLANT FOR PREDICTING EPILEPTIC SEIZURES

CROSS-REFERENCE TO RELATED PATENT APPLICATIONS

This application claims the benefit under 35 USC 119(e) of U.S. Application 60/721,911, filed Sep. 29, 2005, incorporated herein by reference in its entirety.

The United States Government has certain rights in the invention pursuant to Contract No. W-31-109-ENG-38 between the U.S. Department of Energy and the University of Chicago operating Argonne National Laboratory.

The present invention is generally related to a surface acoustic wave device for predicting seizures in a patient. More particularly the invention is related to a surface acoustic wave probe implanted into a patient for sensing temperature changes in the human brain, with certain temperature changes being characteristic of precursors to the onset of a seizure.

Epilepsy is one type of neurological disorder which affects about 1% of the U.S. population, or 2.7 million Americans of all ages. This prevalence figure holds true for all industrialized countries, but it is much higher for underdeveloped countries with rates as high as 10%. Up to 40,000 Americans die each year from seizures in a country where medical care is the most advanced in the world; and this underscores the serious impact of this disease. Most people with epilepsy, although of normal intelligence, are either unemployed or sub-employed due primarily to the unpredictability of seizures. Despite current advances in drug therapy, only 15% of those treated by state of the art medications have neither seizures nor debilitating side effects. The negative impact of epilepsy on the lives of those who suffer from epilepsy and on their families and communities can be considerably lessened if the unpredictability of seizures is removed and innovative alternatives such as non-pharmacological treatments are developed.

Early prediction of the onset of seizures is critical for implementing appropriate prevention measures such as by electrical excitation, cooling or drug therapy. A prediction window of 15 s to 180 s would allow time for effective use of appropriate prevention strategies. There have been attempts to monitor the electrical potentials between a pair of electrodes implanted in the brain to provide direct means of detecting neuronal activity. However, this technique has not been found very reliable because of the dynamic noise in the electrographic signals.

SUMMARY OF THE INVENTION

A surface acoustic wave (SAW) sensor can be used to detect temperature changes in the human brain by implementation into seizure-prone areas of the brain. This is an indirect but a more reliable device and method to detect the onset of seizures with a precursor temperature change that follows commencement of abnormal neuronal activity in the epileptic zone of a patient's brain. For example, a characteristic temperature pattern is an initial dip of about 0.2-1° C. which is then followed by a rapid rise of about 3-4° in the seizure-prone areas of the brain.

The subject SAW sensor can be implanted and configured to operate in a wireless mode and without a battery power source. The wireless SAW sensor includes a delay-line configuration coupled with an RF antenna that communicates with an outside interrogation unit. A transmitting inter-digital transducer (IDT) on the SAW sensor transforms the RF signal from the outside interrogation unit into surface acoustic waves. The waves propagate on the SAW substrate, which is the sensing region. The sound propagation parameters such as phase velocity and delay time vary with temperature. A receiver IDT on the SAW sensor converts the SAW signal into an RF signal, which is then transmitted back to the interrogation unit. The pseudo-wireless version consists of a wired SAW sensor implanted in the brain tissue and connected to a miniature transceiver unit mounted on or under the skull. A telemetry unit interrogates with the transceiver for collecting and monitoring the sensor parameters.

The principal features of the invention therefore include without limitation:

1. Epileptic seizure onset detection is based on the method of monitoring temperature change, which may precede the chaotic electrical signals normally used in prediction of seizure activity;
2. Development of a dual SAW sensor scheme with a very high sensitivity of 1.4 millikelvin; and
3. Design of passive implantable SAW device for wireless operation, without need of a battery power source.

Various aspects, features and advantages of the invention are described hereinafter and these and other improvements will be described in more detail hereinafter, including the drawings described below.

DETAILED DESCRIPTION OF THE PREFERRED EMBODIMENTS

Figure 1:
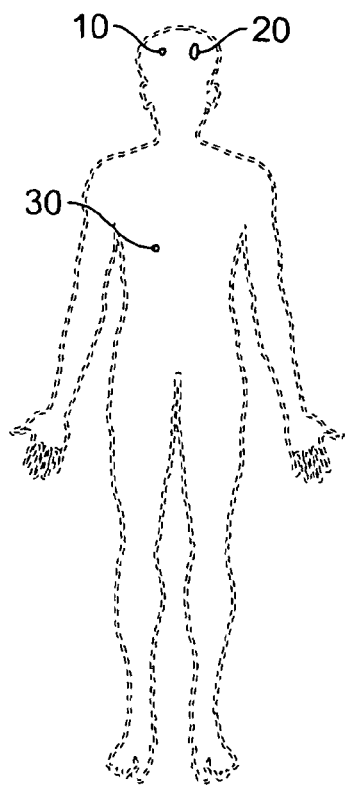
FIG. 1 illustrates an epilepsy control system disposed in a human.

One form of the invention is shown in FIG. 1 in conjunction with use in the human body and a surface acoustic wave ("SAW" hereinafter) sensor 10 is shown generally at 10. As will be discussed hereinafter, a clinician may also choose to include a cooling implant 20 as a means of arresting seizures. In addition, a remote interrogation/control system 30 (hereinafter "control system 30") is shown for control of the SAW sensor 10 and/or the cooling implant 20.

The precursors of a seizure are believed to be manifested by temperature changes in certain parts of the human brain 15. This temperature change can be detected by the SAW sensor 10 and then characteristic data is transmitted to the control system 30 with a telemetric system 40 (see FIG. 2). The control system 30 evaluates the temperature change information and can activate the cooling implant 20 which can help prevent onset of a seizure by cooling the seizure-prone area of the human brain.

Figure 3:
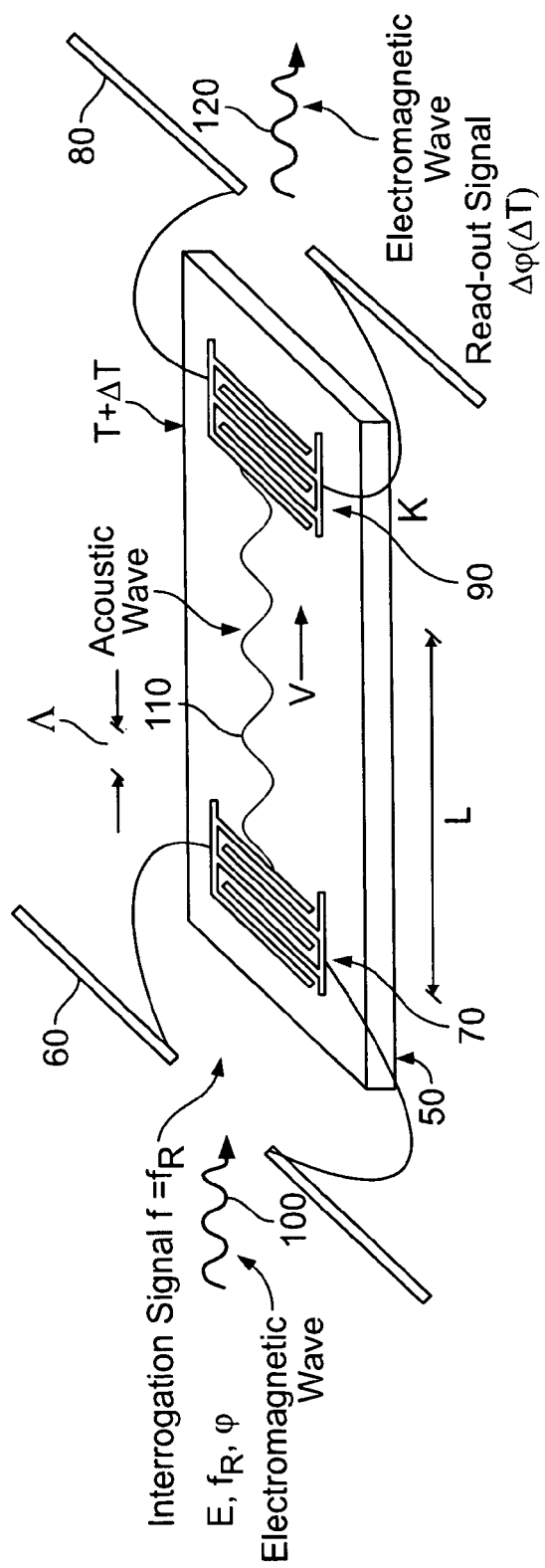
FIG. 3 illustrates a schematic diagram of the SAW sensor.

A more detailed drawing of the SAW sensor 10 is shown in FIG. 3 and includes a substrate 50, first antenna 60 coupled to first interdigital transducer 70 and a second antenna 80 coupled to a second interdigital transducer 90. An interrogation signal 100 excites the first transducer 70 which outputs a surface acoustic wave 110 sensed by the second transducer 90 which provides via the second antenna 80 an output signal 120 characteristic of the acoustic wave sensed. For the system shown in FIG. 4, as the temperature being sensed changes, the phase of an RF signal changes in accordance with a relationship shown hereinafter and explained in detail. The first transducer 70 can function as the measurement sensor and disposed in the epileptogenic region and the second transducer 90 can function as a reference sensor disposed in a non-epileptogenic region. This arrangement minimizes the effect of RF source instabilities, corrects for the background fluctuations in pressure, motions, etc., maximizes the difference in temperature between the two regions (epileptogenic and non-epileptogenic regions), and allows for longer integration of signals and in turn providing higher sensitivity. Or, the reference sensor 90 may be kept in a constant temperature box outside the brain and the measurement sensor 70 in the brain. This arrangement amplifies the temperature changes in the brain with respect to a fixed temperature with attendant benefits of longer integration, etc.

Use of the SAW sensor 10 is then based on varying conditions of propagation of surface acoustic waves in the substrate 50 when temperature, pressure, electric field and mechanical load change. Linear coefficients obtained for the measurable changes from different physical effects are given in Table 1:

TABLE 1

| Physical value | Linear coefficient |
| --- | --- |
| Temperature | Up to 100 ppm/K |
| Pressure | 2 ppm/kPa |
| Mass loading | 30 ppm/µg · cm$^2$ |
| Voltage | 1 ppm/V |
| Electric field strength | 30 ppm/V · µm$^{-1}$ |

As can be seen by the sensitivity shown in Table 1, the temperature (T) can undergo substantial changes over a temperature value range 15-42° C. The principle of temperature measurement with the use of the SAW sensor 10 can be compared to characteristics of the SAW sensor 10 exciting an electric signal. If the substrate temperature changes, the following signal parameters therefore vary:

Amplitude;

Delay period;

Phase;

Resonance frequency.

Figure 4:
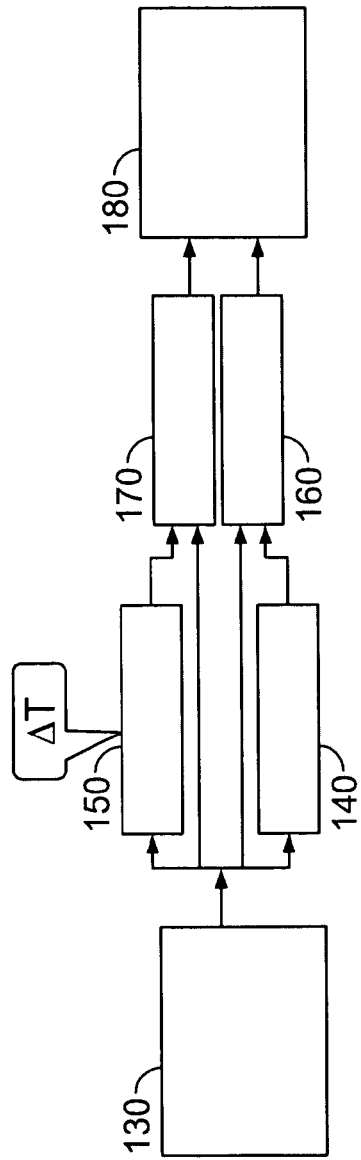
FIG. 4 illustrates a schematic of the phase method of operating the SAW sensor using a dual sensor arrangement.

As shown in FIG. 4, a generator 130, preferably operated at 439-429 MHz, which is linearly modulated with an inside frequency bandwidth of the SAW sensor 10, is used as part of the measurement scheme. Generator output signals are passed to the SAW sensor 10 and then mixers. The SAW sensor "ref" box 140 has a delay time $t_1$ and its constant temperature is $T_0$. SAW sensor "work" box 150 has delay time $t_2$ and measures temperature change $\Delta T$ with phase sensitivity $$S_t^{\Delta \varphi} = \frac{\partial \varphi}{\partial T}$$

(phase degree of arc/° C.). A frequency modulated (FM) reference signal is passed to both of the SAW sensors 10 simultaneously:

$$E_0(\tau) = E_0 \cos 2\pi \left( \left( f_0 + \frac{b\tau}{2} \right) \tau + \varphi_0 \right)$$

Echo-signal from each of the SAW sensors 10 is passed to mixer 160 or 170 and then to a signal processing board 180:

$$E_1(\tau) = E_1 \cos 2\pi \left( \left( f_0 + \frac{b(\tau - t_1)}{2} \right) \tau + \varphi_0 \right)$$

$$E_2(\tau) = E_2 \cos 2\pi \left( \left( f_0 + \frac{b(\tau - t_2)}{2} \right) \tau + \varphi_0 + \frac{1}{360} S_T^{\Delta \varphi} \cdot \Delta T \right)$$

At this moment reference signals also pass to the mixers:

$$E_{01}(\tau) = E_{01}\cos 2\pi\left(\left(f_0 + \frac{b\tau}{2}\right)\tau + \varphi_0\right)$$

$$E_{02}(\tau) = E_{02}\cos 2\pi\left(\left(f_0 + \frac{b\tau}{2}\right)\tau + \varphi_0\right)$$

At the nonlinear mixers output we obtain signals at the intermediate frequencies $bt_1/2$ and $bt_2/2$:

$$A_1(\tau) = A_1\cos 2\pi\left(\frac{bt_1}{2}\tau\right)$$

$$A_2(\tau) = A_2\cos 2\pi\left(\frac{bt_2}{2}\tau + \frac{1}{360}S_T^{\Delta\varphi}\cdot\Delta T\right)$$

Thus the methodology lets us transfer the phase shift $S_T^{\Delta\varphi}\cdot\Delta T$ into the low frequency region. After digitizing these low frequency signals with the help of microcontroller, one can determine the value of the SAW sensor substrate temperature.

Considering interrelation of time delay, $t_0$, in the SAW sensor 10, which appears as a result of relation between $A_2(\tau)$ and other physical values, an intermediate frequency $\Omega_\phi = bt_2/2$ should be low enough to provide an opportunity to measure phase shift with the required accuracy. On the other hand, it must provide the required system operation speed (on the basis of the up-date available data on development of epileptic seizure, this should be about $\leq 1$ sec. $-/1/$). Coefficient $b \approx \Delta\omega\cdot\Omega_\omega$ is determined by the acoustic width of the SAW sensor bandwidth $(\Delta\omega)$ and operation frequency of the saw-tooth voltage generator $(\Omega_\omega)$. To estimate delay time $t_2$ one can take the signal delay time, $t_0$, in the SAW sensor 10.

We can then obtain the relationship, linking parameters of the scheme $(\Omega_\omega)$, SAW sensor $(\Delta\omega$ and $t_0)$ and the requirements, imposed on accuracy and operational speed of the temperature sensor $(\Omega_\phi)$:

$$\Omega_\phi \sim \Omega_\omega\cdot\Delta\omega\cdot t_0$$

One can see that $t_0$ should not be considered in isolation from other characteristics of the system. In our case for $\Omega_\omega \approx 1$ kHz, $\Delta\omega \approx 10$ MHz, $t_0 \approx 0.2$ us (for conventional BIOFIL sensors) we obtain $\Omega_\omega \sim 2$ kHz, which seems an optimal value both from the viewpoint of sensitivity and operational speed.

Consequently, delay period (t) at acoustic signal propagation depends on the SAW velocity (v), distance between receiver and emitter (L) which is the distance between the first transducer 70 and the second transducer 90:

$$t = L/v$$

One the one hand temperature rise causes an increase of delay period at the expense of the substrate thermal expansion (L) and on the other hand, causes a delay period decrease at the expense of rise of sound velocity (v). Temperature dependence of delay period is determined by the temperature coefficient:

$$\alpha = \frac{1}{t}\frac{dt}{dT} = \frac{1}{L}\frac{dL}{dT} - \frac{1}{v}\frac{dv}{dT}$$

Under our conditions $\alpha$ does not depend on distance L and temperature.

Example values of linear temperature coefficient $\alpha$ for different crystals at room temperature are given in Table 2:

TABLE 2

| Crystal | Cut type | α |
|---|---|---|
| LiNbO₃ | 128 Y/X | 75 ppm/K |
|  | Y/Z | 94 ppm/K |
| LiTaO₃ | X/112Y | 18 ppm/K |
|  | 36 Y/X | 30 ppm/K |
| La₃Ga₅SiO₁₄ | X/Y | 24 ppm/K |
| SiO₂ | ST-X | 0 ppm/K |

One can see from these values that for the SAW sensor 10, it is more preferable to use substrates made from niobate and lithium. This material characteristics are presented in Table 3.

TABLE 3

| | type of cut | |
|---|---|---|
| | Y/Z | 128° Y/X |
| propagation velocity m/s | 3488 | 3992 |
| piezoelectric bond parameter*) $\Delta v/v$, % | 2.41 | 2.72 |
| Damping at 1 GHz, dB/mcs | 1.07 | |
| bond with volume waves | Strong | weak |

*⁾is effect of changing wave velocity because of surface metallization: $\Delta v = v_m - v_0$, where $v_0$ is velocity on free surface, $v_m$ is velocity on metallized surface, a large value $\Delta v/v$ usually allows to get small introduced losses.

Changing of the substrate temperature by value $\Delta T$, causes the delay period $t_0$ to be:

$$\Delta t \approx \alpha t_0 \Delta T$$

This delay value of the existing SAW devices is $t_0 \sim 1$ microsec, with a required accuracy of temperature measurement $\Delta T=0.1K$, $\alpha=94\cdot 10^{-6} K^{-1}$ which is why the expected variation of delay period is:

$$t \approx 94\cdot 10^{-6} \times 1\cdot 10^{-6} \times 0.1 \approx 1\cdot 10^{-11} s.$$

This accuracy in measurement of time intervals with the help of electronics currently offered on the market cannot be achieved. This is why a carrier frequency phase change measurement which appears from time delay changing is a fundamental advantage of the SAW sensor 10. When the delay period changes about $\Delta t=1\cdot 10^{-11}$ s and the exciting signal frequency $f=430$ MHz/ . . . /, the phase shift of the read-out signal relative to the exiting signal is:

$$\Delta\phi \approx f\Delta t\cdot 360° = 4.3\cdot 10^8 \times 1\cdot 10^{-11} \times 360° \approx 1.5°$$

The existing electronics market gives wide opportunities for creating devices with carrying frequency $F_c \leq 100$ MHz. That is why in order to measure phase shift $\Delta\phi \sim 1.5°$, one should reduce the frequency of the signal, read out from the SAW sensor 10 by the heterodyning method for at least the value:

$$f_g < F_c \frac{\Delta\varphi}{360°} = 10^8 \frac{1.5}{360} \approx 4\cdot 10^5 = 0.4 MHz$$

This task can be solved on the base of existing elements. To develop the SAW temperature sensor 10 for phase shift measurements it is necessary to measure experimentally an exact value of certain sensor sensitivity (phase sensitivity):

$$S_T^{\Delta\varphi} = \frac{\partial(\Delta\varphi)}{\partial T}$$

In order to understand the physical structure of the SAW sensor 10, the most significant physical characteristics are tabulated in Table 4 for typical values.

TABLE 4

| | Typical value | Devices for measurement |
|---|---|---|
| Operation frequency | 100 ÷ 500 MHz | generator, oscilloscope |
| bandwidth | ≈10 MHz | generator, oscilloscope |
| Delay period | 0.2 ÷ 10 us | High speed switch, oscilloscope, generator |
| Depression coefficient in the SAW sensor | 1 ÷ 20 times | Generator, oscilloscope |
| Phase sensitivity | 1 ÷ 200 phase degree of arc/° C. | Thermal stable box, thermometer, temperature varying device |

As noted hereinbefore, the general characteristic for determining an efficiency of the SAW sensor 10 as a temperature sensor, is principally phase sensitivity or, in other words, temperature dependence of the SAW sensor 10 output signal phase shift relative to input signal at operation frequency.

Figure 5A:
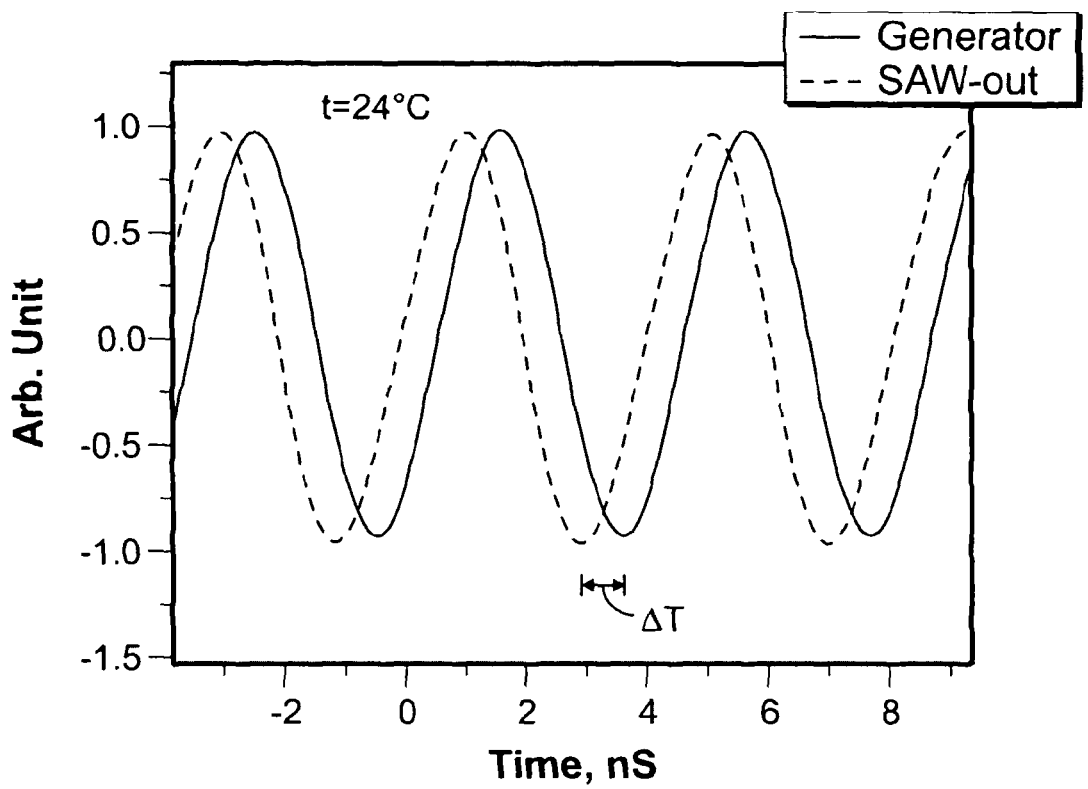
FIG. 5A illustrates input and output oscillograms at T=24° C. for measurement of the SAW sensor
Figure 5B:
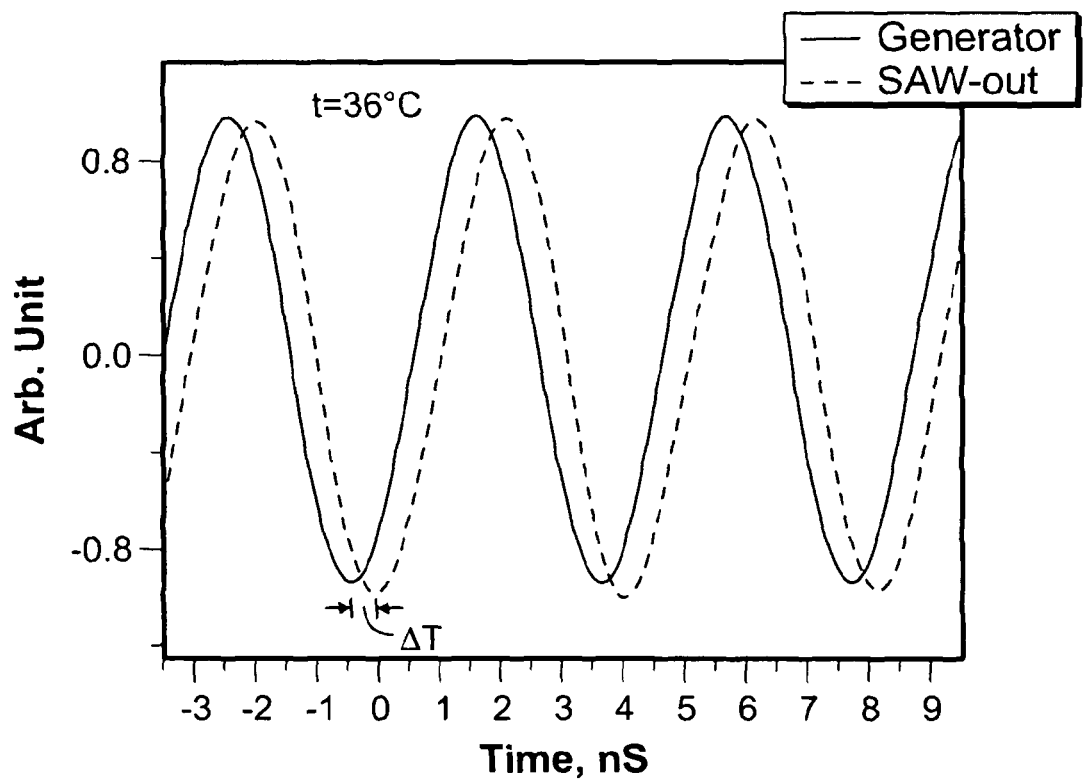
FIG. 5B illustrates the results for T=36° C.

Measurements of phase sensitivity at operation frequency were carried out on test benches, equipped at BIOFIL, in the following order: A sinusoid signal was applied on the SAW sensor input for the resonant conditions for the given temperature frequency, $f_R$. Input and output signals were recorded by conventional oscilloscopes TDS 3054 or TDS 5104. The temperature of the SAW sensor 10 was measured by a standard thermocouple temperature measuring device with accuracy ±3° C., or a diode measuring device, specially fabricated by BIOFIL, with an accuracy ±0.05° C. The SAW sensor body was heated up (by a thermal fan) or cooled off (such as by liquid nitrogen) to the given temperature. The input and output signal typical oscillograms are presented in FIGS. 5A and 5B for two different temperatures.

The time shift of output signal relative to input signal was measured by an oscilloscope. Value $\Delta\varphi$ was calculated from formula:

$$\Delta\varphi = \frac{360 \cdot \Delta T}{T}$$

Figure 6A:
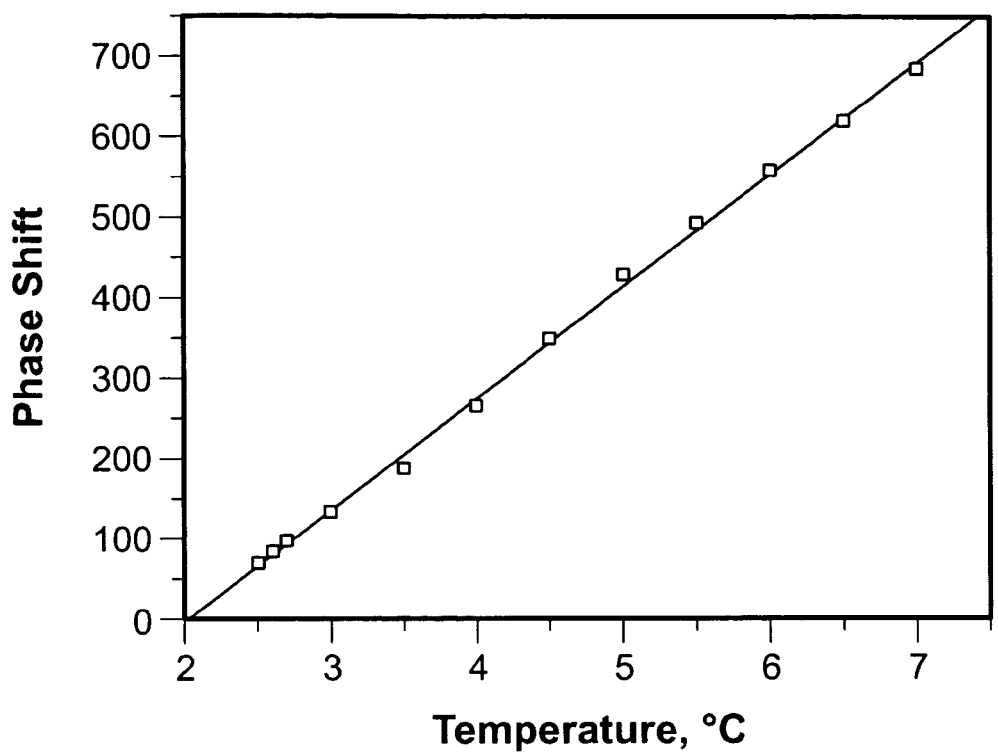
FIG. 6A illustrates SAW sensor temperature-phase shift dependence for a delay line at 434 MHz and FIG. 6B illustrates the dependence for using in a filter mode at 172 MHz.
Figure 6B:
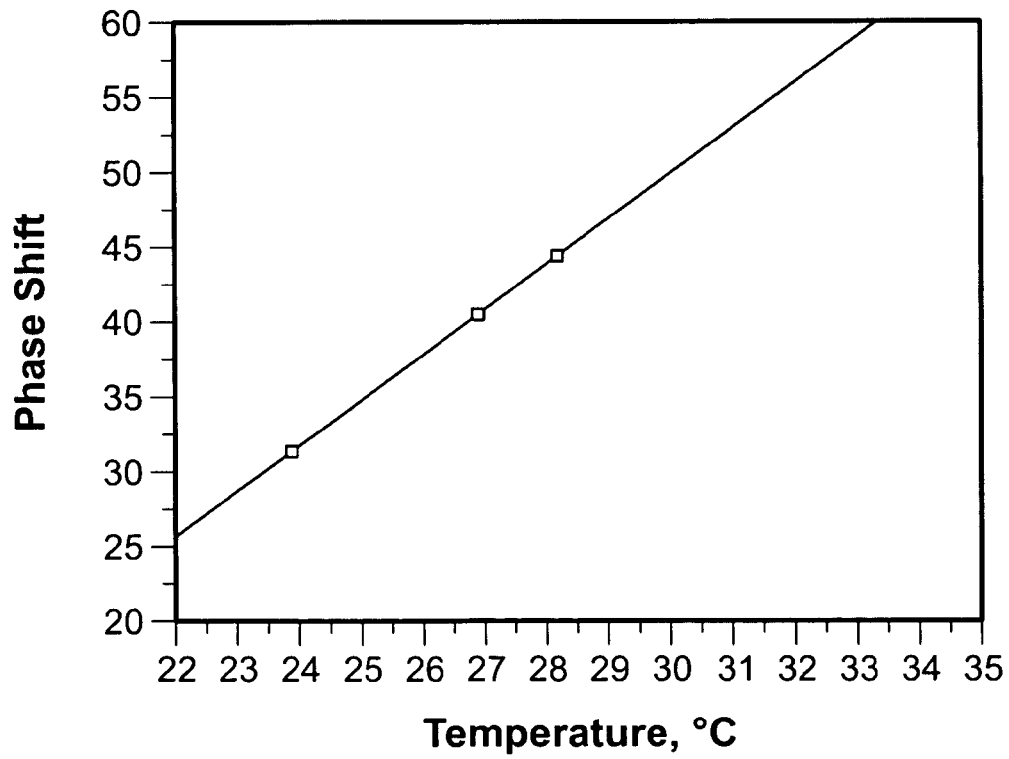

$\Delta T$ is the output signal time shift (SAW-out) relative to Input signal (generator), and T is the input signal period ($1/f_R$). Computer processing of waveforms, obtained with the use of digital oscilloscope, allows one to carry out phase measurements with error ~0.2°. At the sampled temperature ranges one can notice linear dependence between phase shift value and temperature for both types of the SAW sensors 10 (see FIGS. 6A and 6B) and phase sensitivity values in Table 5.

TABLE 5

| Phase sensitivity values, calculated on experimental data: | | |
|---|---|---|
| Sensor | Operation frequency | Phase sensitivity, Phase degree of arc/° C. |
| ANL (resonator type) | 245 MHz | 9.4 ± 0.9 |
| "Etalon" (filter) | 172 MHz | 3.0 ± 0.2 |
| "Etalon" (filter) | 434 MHz | " |
| "Etalon" (delay line) | 434 MHz | 144 ± 5 |

For the SAW sensor 10, delay period is quite an important characteristic, as it determines intermediate frequency value.

Figure 7A:
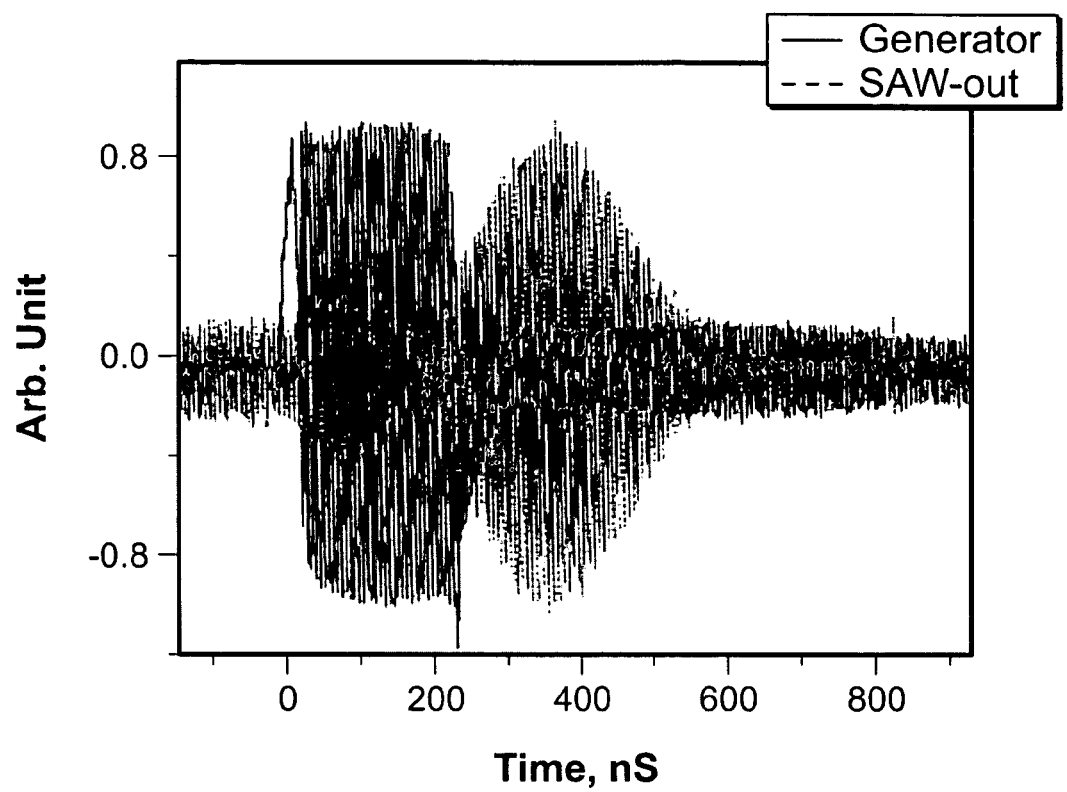
FIG. 7A illustrates typical pulsed signal oscillograms for measurements of SAW sensor delay periods with a filter mode at 172 MHz and FIG. 7B illustrates an oscillogram for a delay line at 434 MHz.
Figure 7B:
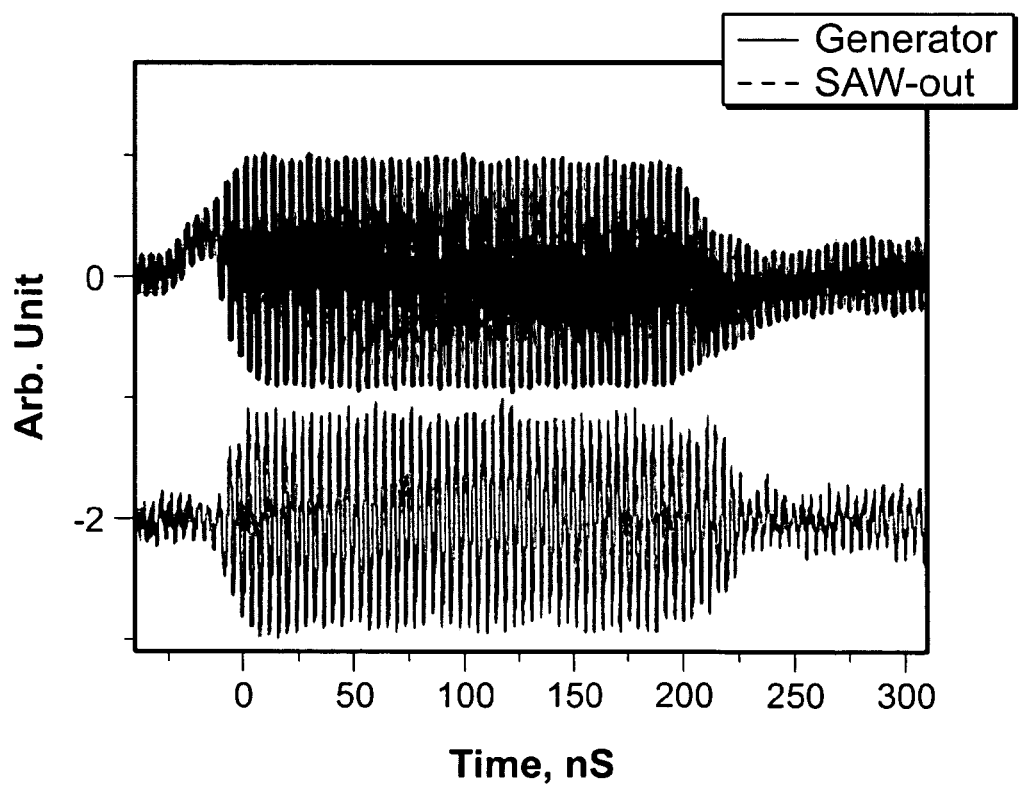

For measurement of delay period, t, at the SAW sensor 10, an input pulsed signal filled by sinusoid at frequency $f_R$, was applied. The SAW sensor 10 input and output values were recorded by oscilloscope. The time period between these two signals (see FIGS. 7A and 7B and Table 6) is equal to delay period, t, at the SAW sensor 10.

TABLE 6

| sensor | Operation frequency | Delay period t |
|---|---|---|
| ANL (resonator type) | 245 MHz | <20 ns |
| "Etalon" (filter) | 172 MHz | (250 ± 25) ns |
| "Etalon" (filter) | 434 MHz | " |
| "Etalon" (delay line) | 434 MHz | 10.4 ± 0.5 |

Error is connected with accuracy of determining the proper time interval duration with the help of oscilloscope, and such error can be explained by the fact that accuracy of determining the proper time interval duration with the help of oscilloscope is not high enough.

Figure 8A:
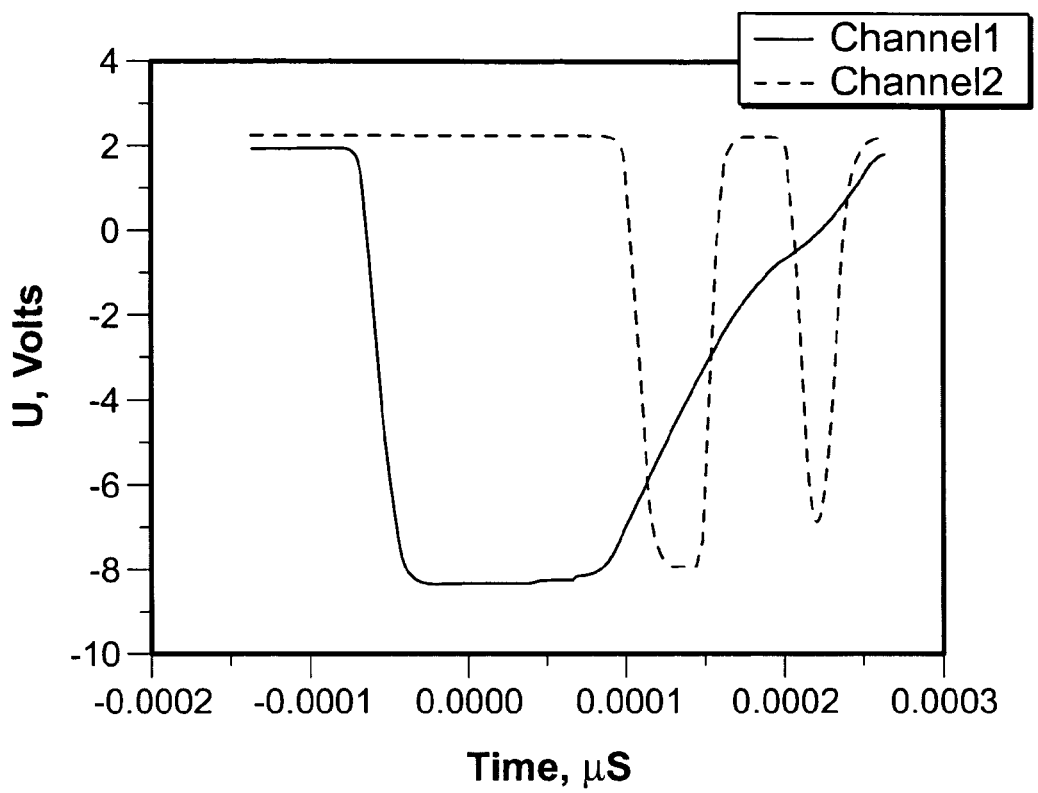
FIG. 8A illustrates a signal oscillogram at the intermediate frequency from a reference channel (Channel 1) at 0° C. and measurement (Channel 2) of the SAW sensor at a measurement temperature of 41° C.
Figure 8B:
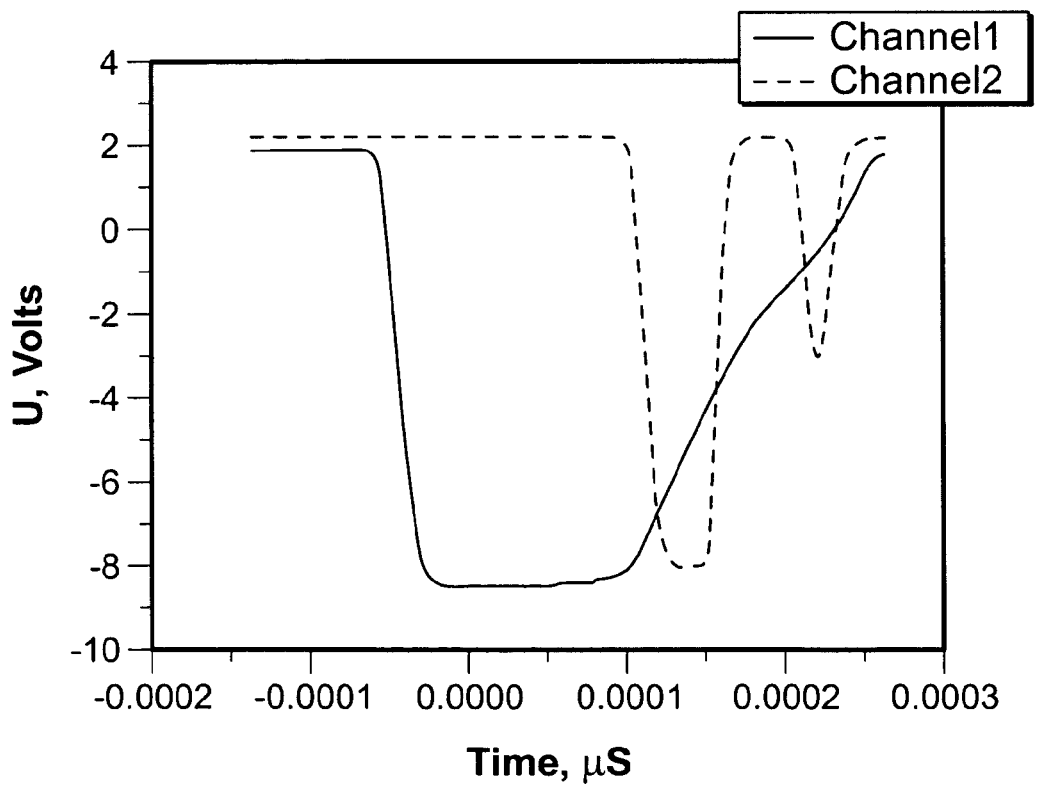
FIG. 8B shows the oscillogram at a temperature of 44° C.

An HF oscillator (HFO) with FM produces sinusoidal voltage in the frequency range 300 to 900 MHz. Amplifying on the previous representation and as stated before, the basis of temperature measurement is most preferably the measurement of phase shift of the sensor signal response at an intermediate frequency. The signal from the similar SAW sensor 10, in the case where the temperature is constant, is used as a reference signal. FIGS. 8A and 8B present typical oscillograms.

Figure 9A:
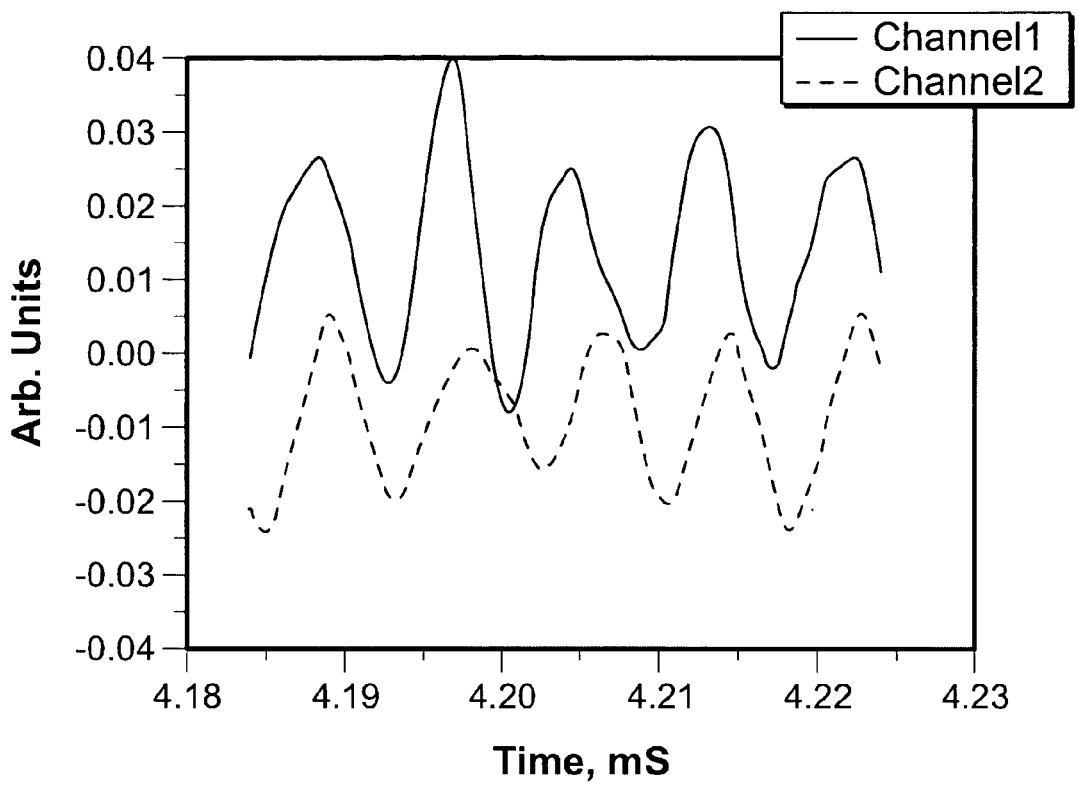
FIG. 9A illustrates signal oscillograms at an intermediate frequency from the reference (full line) and measured values (dotted line) for the SAW sensor with a filter type sensor and carrier frequency at 172 MHz.
Figure 9B:
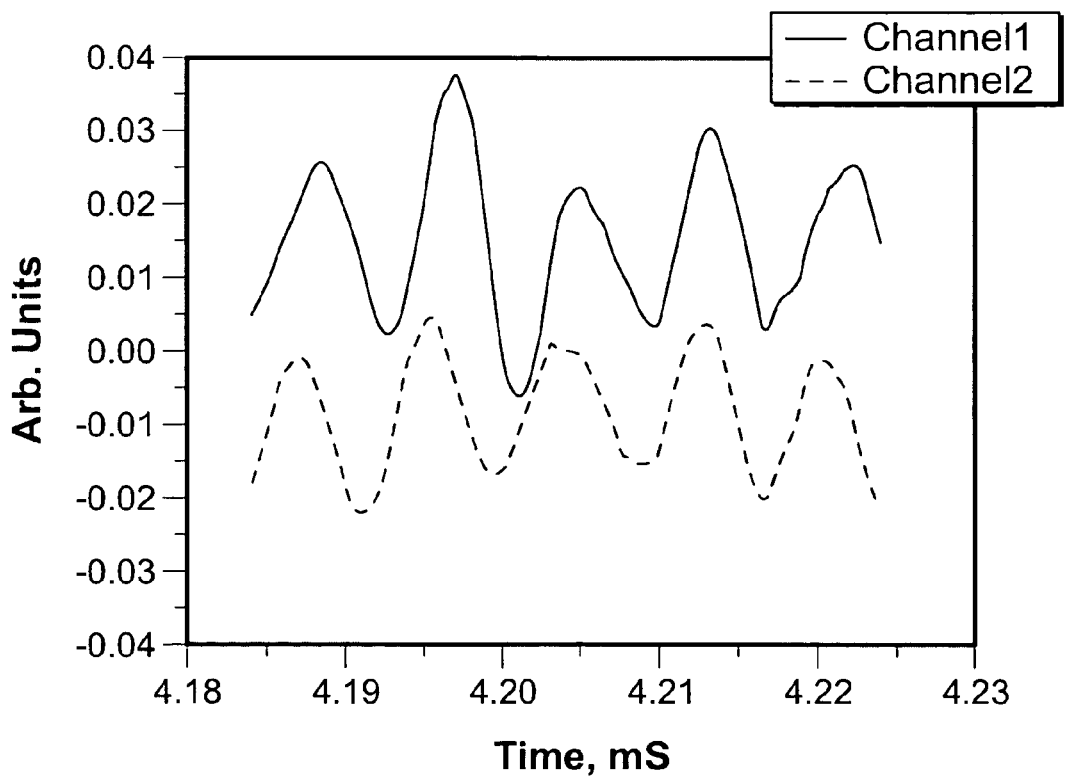
FIG. 9B shows the change of phase shift with reference to FIG. 9A when the measurement sensor was heated by a filament lamp.

The conditions, for which the oscillograms in FIGS. 9A and 9B are obtained, are presented in Table 7.

TABLE 7

| | FIG. 9A | FIG. 9B |
|---|---|---|
| Sensor type | Filter | Delay line |
| Manufacturer | "Etalon" | "Etalon" |
| operation frequency | 172 MHz | 434 MHz |
| frequency modulation range | 172 ... 177 MHz | 420 ... 440 MHz |
| frequency modulation frequency | 1 kHz | 0.66 kHz |
| oscillator output voltage | 500 mV | 200 mV |
| Intermediate frequency, of order | 1 kHz | 170 kHz |

Figure 10:
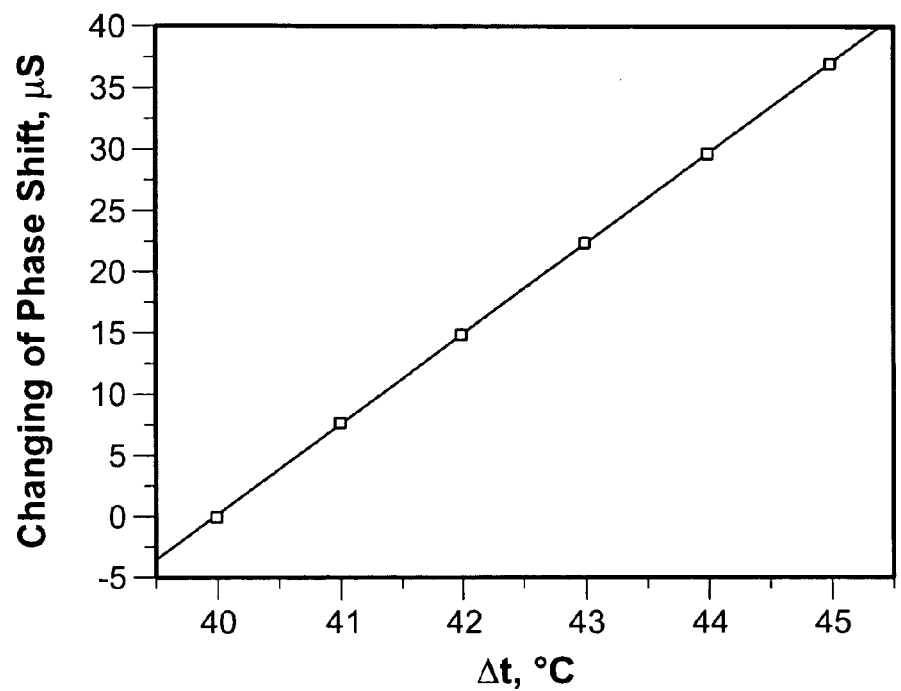
FIG. 10 shows variation in phase difference in relation to temperature differences from FIGS. 9A and 9B.

FIG. 10 presents the results of absolute calibration of the sensor, which oscillograms are shown in FIGS. 9A and 9B. The variation in phase difference is therefore shown in relation to temperature differences.

Figure 11:
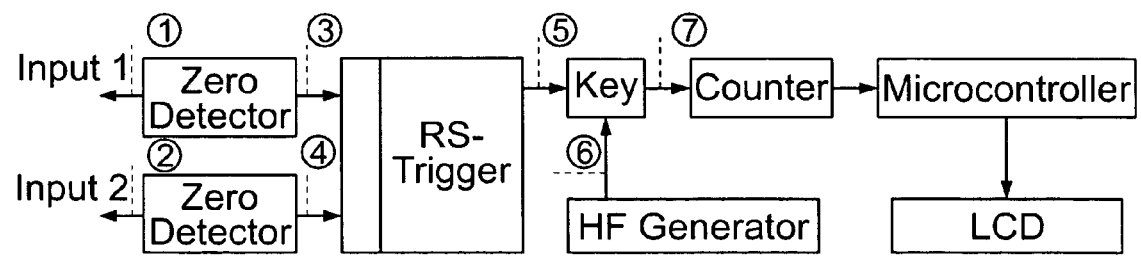
FIG. 11 illustrates a block diagram of a phase shift to temperature converter.

One can see that the dependence between phase shift and temperature is directly proportional. The achieved sensitivity is of the order of 0.1° C. and evidently is caused by operational non-stabilities of the temperature sensor electronic circuit. The "phase shift—temperature" converter is specially designed in BIOFIL for measurement of phase shift of two sinusoidal intermediate frequency signals and its proportional conversion into temperature. The converter block diagram is shown in FIG. 11.

The proposed method readily enables the digital phase shift measurement. In such phase shift measurements one signal is taken as a reference one (input 1). As shown in FIG. 11, the second signal phase shift (input 2) is counted out relative to the first signal. The signals (①and ②) fall at the null detectors input. At the detector output in the moment of changing signal signs, the pulses (③ and ④) appear, and they set and then release RS-trigger. At the same time the pulse, which is shaped at the RS trigger output (⑤) unlocks the switch and lets the HF oscillator (⑥) pulse sequence pass at the counter ((7)). The number of pulses, passing through the counter, is in the proportion to time difference between moments of passing the researched signals through null point, that is signal phase difference. The microcontroller reads from the counter a pulse number and outputs on a liquid crystal display the temperature value in degrees.

Figure 12A:
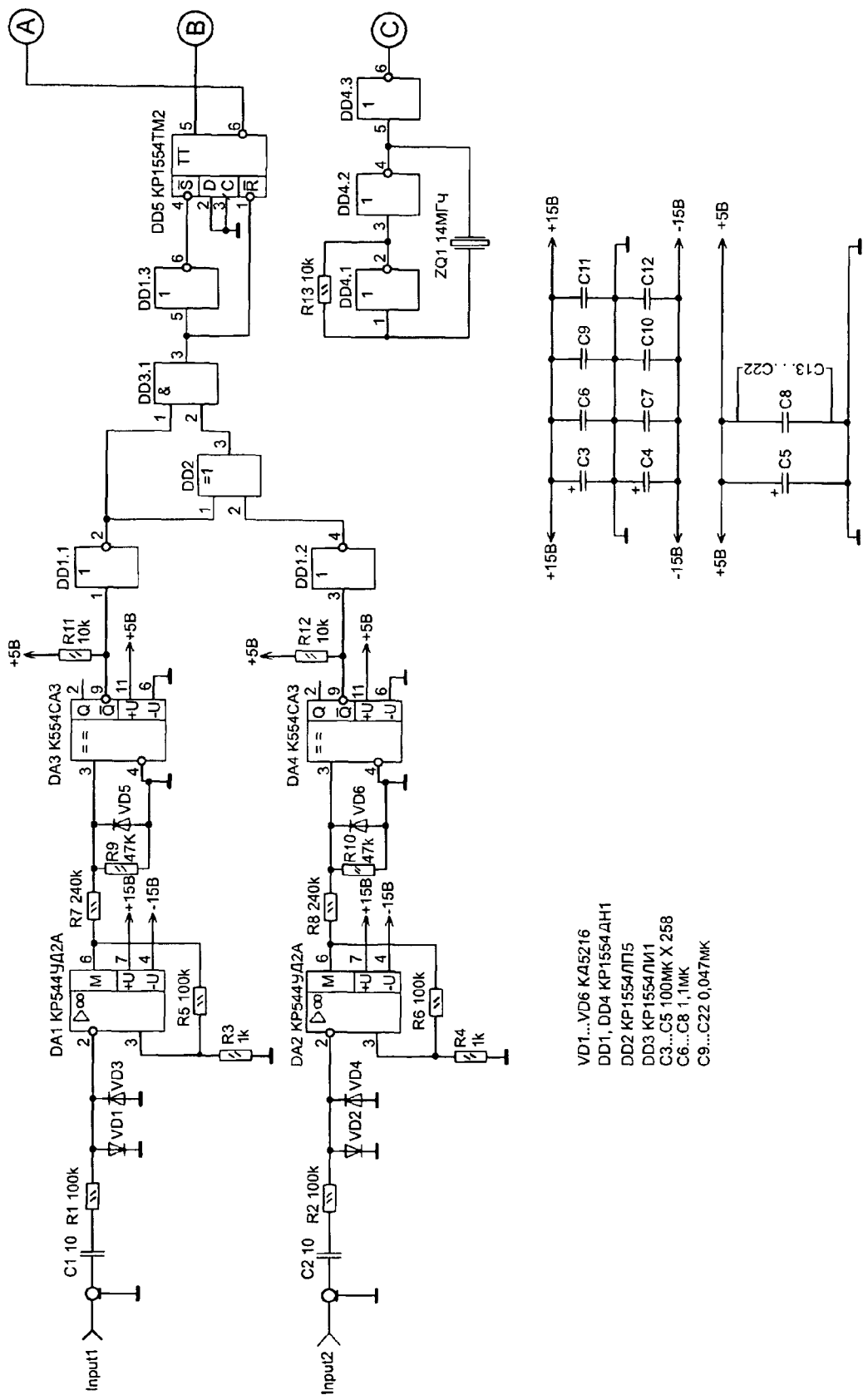
FIGS. 12A and 12B illustrate in a split drawing a phase shift-temperature converter basic circuit.
Figure 12B:
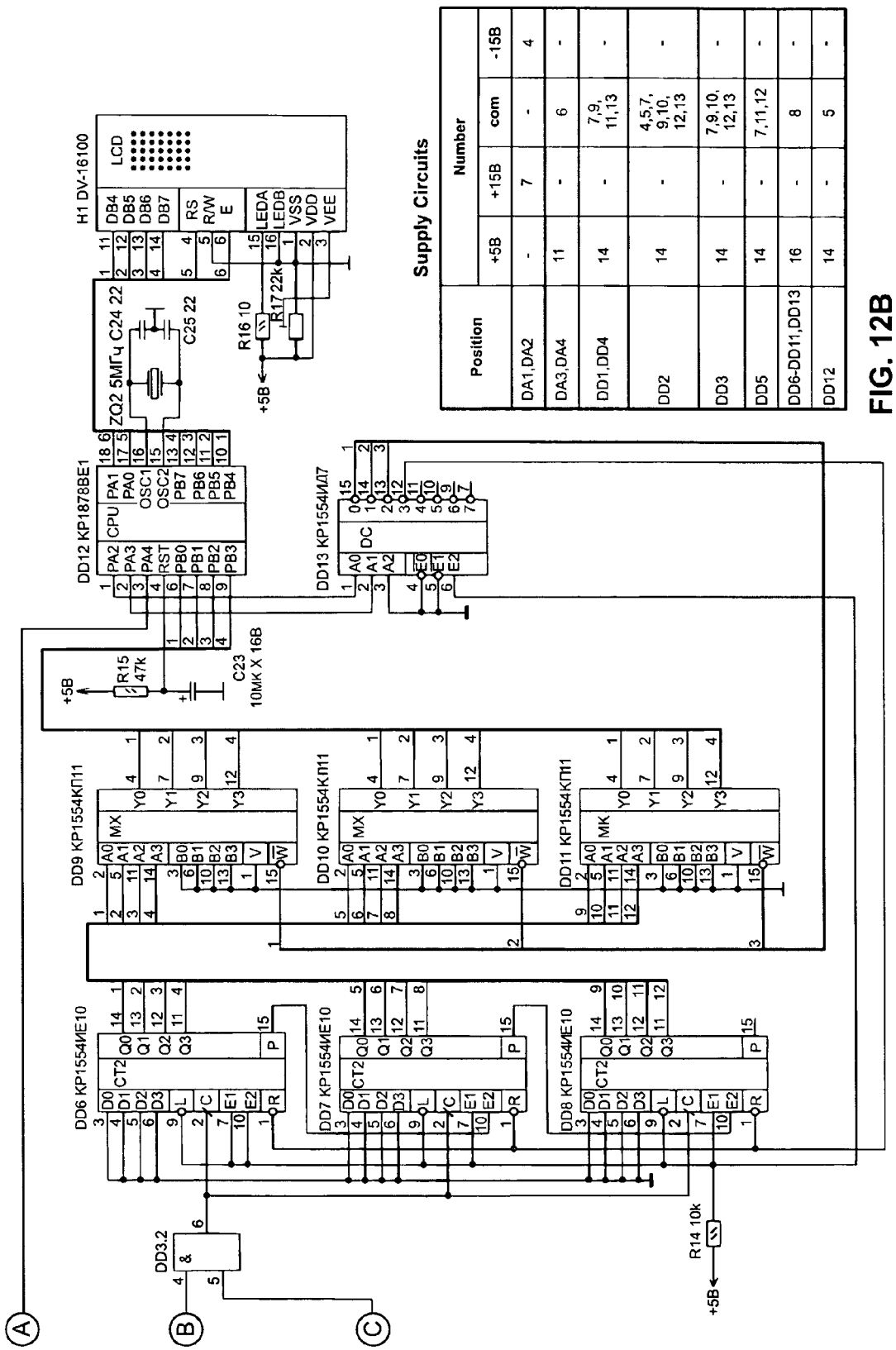

FIG. 12 illustrates the converter basic circuit. Null detectors were assembled on the base of operation amplifier (OA) DA1, comparator DA3 and operation amplifier (OA) DA2, comparator DA4 correspondingly. RS trigger was made on the base of DD5 chip. The switch is based on DD3.2 element. HF oscillator is based on DD4.1, DD4.2 and DD4.3 elements. 12 digit cascade counter was fabricated using DD6, DD7 and DD8 chips. The microcontroller was fabricated using DD12. The liquid crystal display is a single line indicator, which consists of 16 cells and shows temperature.

The intermediate frequency reference signal goes at (OA) DA1, which is switched on in accordance with the inverting Schmidt trigger circuit. The Schmidt trigger converts analog signal into pulse sequence of the same frequency and phase. Bipolar output signal of the Schmidt trigger goes at DA3 comparator, which converts bipolar signal into single polar logical signal in the TTL levels, necessary for digital chips. The second signal of the same frequency, sent at DA2 OA input, is converted in the same way. Digital signals, obtained from outputs of DA3 and DA4 comparators, commutate RS trigger DD5. On the RS trigger output a square pulse is generated. Its duration is equal to time difference between moments of passing the researched signals through null point, which is in proportion with signal phase difference. From the RS trigger output the pulse goes to the DD3.2 electronic switch where controls passing through the switch of the crystal oscillator pulses. The crystal oscillator uses DD4.1, DD4.2 and DD4.3 elements. In such a way the null detector pulses are stuffed by the HF oscillator pulses, which are counted by 12 digit counter DD6, DD7, DD8. The DD12 microcontroller reads in series on four digits the data from the counter through DD9, DD10 and DD11 multiplexers, by sampling them with the help of DD13 decoder. Then the microcontroller converts the obtained data and outputs on a liquid crystal display the temperature value in degrees.

Figure 2:
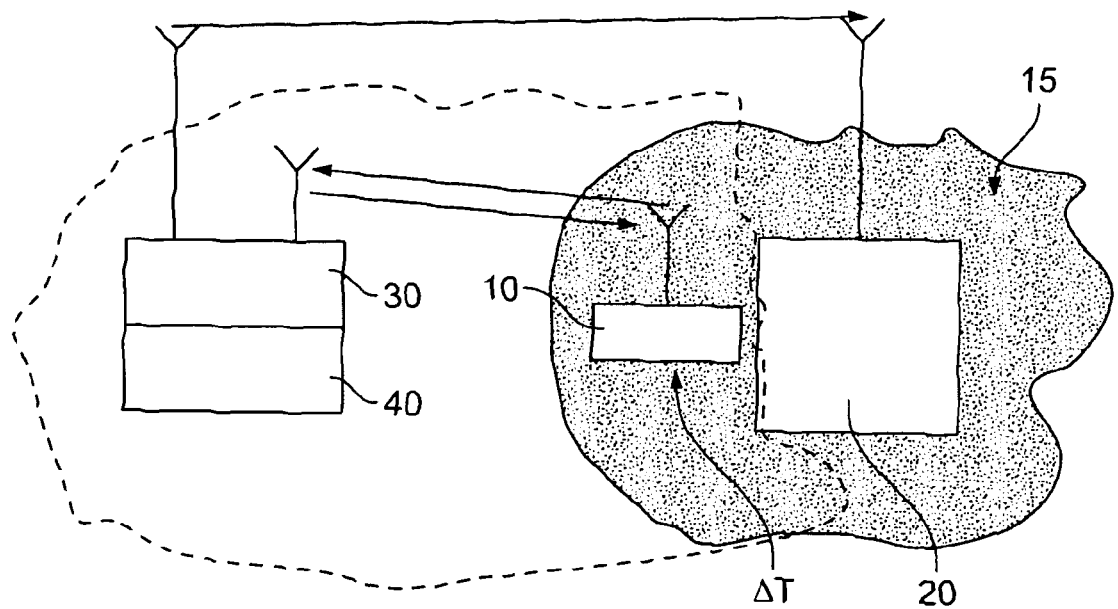
FIG. 2 illustrates details of the control system of FIG. 1.
Figure 13:
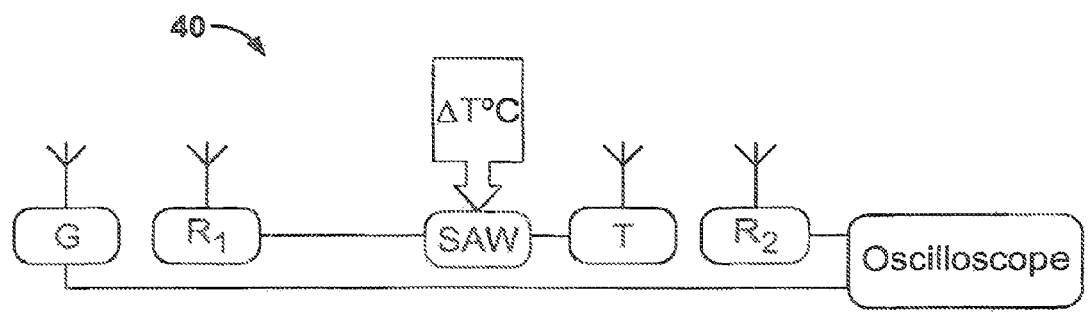
FIG. 13 illustrates a schematic of a telemetry system at a frequency of 434 MHz (dipole antenna) where G is a high frequency generator with antenna; $R_1$ and $R_2$ are receiving antennae and T is a transmitting antenna.

The telemetry system 40 of FIG. 2 was established according to the embodiment presented in FIG. 13. The operation frequency was preferably 434 MHz. Lines in FIG. 13 represent galvanic coupling. All antennae were made in a similar way and they were dipoles of 17 cm length, which is about ¼ of the wavelength. The distance between the antennae was about several centimeters. A symmetric SAW filter with resonance frequency 434 MHz was used as the SAW sensor 10. The oscillation phase shift at changing the SAW sensor temperature was registered by a Tektronix 3054 oscillograph with the pass bandwidth up to 500 MHz.

Figure 14:
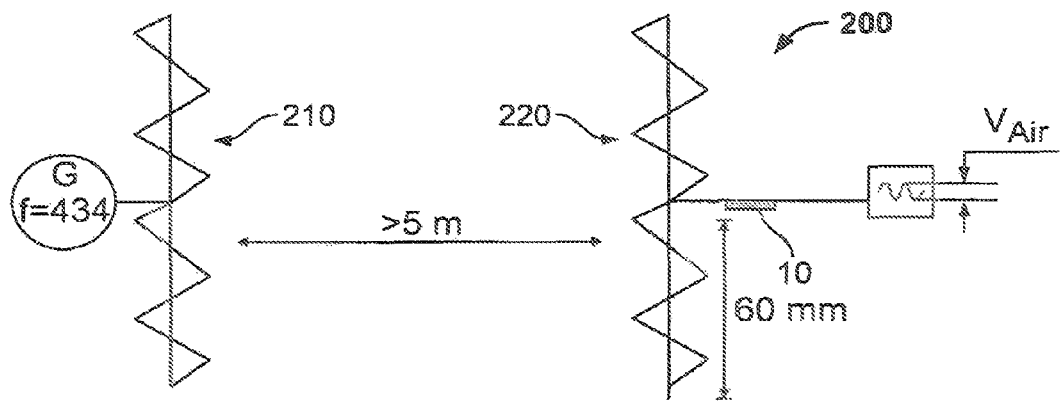
FIG. 14 illustrates a telemetry system at 434 MHz (zigzag antennae)

Development of the antenna design 200 (see FIG. 14) for 434 MHz was carried out with the help of a MMANA v.0.11 program (which is a freely distributed conventional program). For antenna development particular attention was given to fulfilling the requirements for the antenna input resistance, which must be close to the value of about 50Ω. The matching elements (capacity and inductivity) shall have a small value. These features are related to the fact the SAW sensor 10 has input resistance of 50Ω and capacity of about 5 pF.

Two zig-zag antennas 210 and 220 were developed and investigated:
1. The dimensions were 130×65×1 mm$^3$ and the matching device to operate with coaxial cable; and
2. The dimensions were 130×65×1 mm$^3$, without the matching device with purely active resistance in 50Ω for direct connection to the SAW sensor 10.

With the help of the second antenna 220 it was provided the length was no less than 3 meters. At a power of ≈20 mW on the transmitting antenna, the oscillograph signal was equal to ~1 mV.

Flagpole antennas operate with less efficiency than frame antennas in the absorbing media (brain substance falls in this category). That is why the variant of single-turn frame antenna was chosen for the preferred design. During the design, one goal was reducing the reactive component of the current because it does not take part in energy conversion.

The antenna design 200 was developed with the help of MMANA v.0.11 program (which is freely distributed). The shape was given as a regular octagon with 24 mm equivalent diameter. Diameter of the wire (copper without surface insulation) was equal to 2.5 mm. The antenna parameters are the following:

Input resistance (0.102+0.004·)Ω
Current (9.78+0.35·i) A at the input voltage 1V
Standing wave ratio 489 (the cable wave resistance 50Ω)
Gain factor 3.1 dB
Parameters of agreement (cable with wave resistance 50Ω): capacity≈160 pF in parallel, induction≈0.001 µF—sequentially
Directional radiation pattern of this antenna is a toroid and practically does not contain "dead zones".

The measurements, conducted with this antenna 200 demonstrated that its characteristics allow obtaining an excess over the noise level of 10 dB at a distance between the antennas in the air of about ≈100 mm.

Developing antennas of this type one should take into account the fact that the frame antenna efficiency usually is 0.001-0.0001, the antenna input resistance (about 0.1Ω) is in rather poor agreement with wave resistance of receiving and transmitting devices (about 50Ω).

Figure 15:
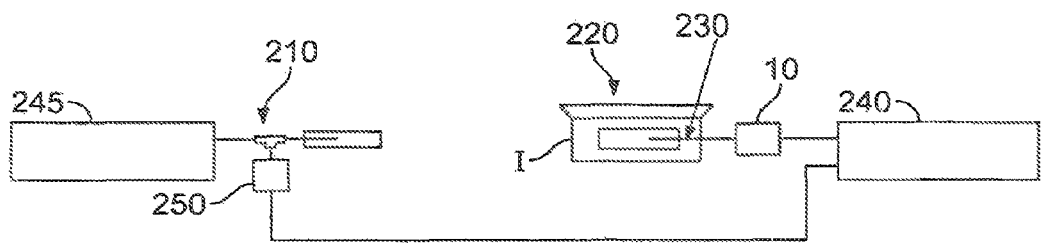
FIG. 15 illustrates components of a simulation system for sensing temperature deviations.

Since the SAW sensor 10 will be implanted into the brain, one of the telemetry system antennas described hereinbefore will be submerged in the brain, which dielectric properties significantly differ from the air properties. To estimate the influence of these factors a set of experiments was carried out. The experimental layout is presented in FIG. 15. The receiving antenna 230 of the SAW sensor 10 was covered with dielectric protecting coating. Than the antenna 230 was submerged in the brain medium simulator (I, table salt water solution, concentration from 0 to 3.3% per mass, the volume of liquid is 3 liters). The signal from the SAW sensor 10 is passed to the input of an oscillograph 240, and the oscillograph start-up synchronizing was performed by the signal from the generator 245. To reduce a level of parasite refraction a voltage divider 250 was used.

The experimental results are tabulated at Table 8:

TABLE 8

| No | Experimental conditions | reduction |
|---|---|---|
| 1 | Air medium | 1.0 |
| 2 | Distillated water | 24.6 |
| 3 | Dielectric protecting coating + air medium | 15.0 |
| 4 | Dielectric protecting coating + simulating medium | 36.0 |

Figure 16:
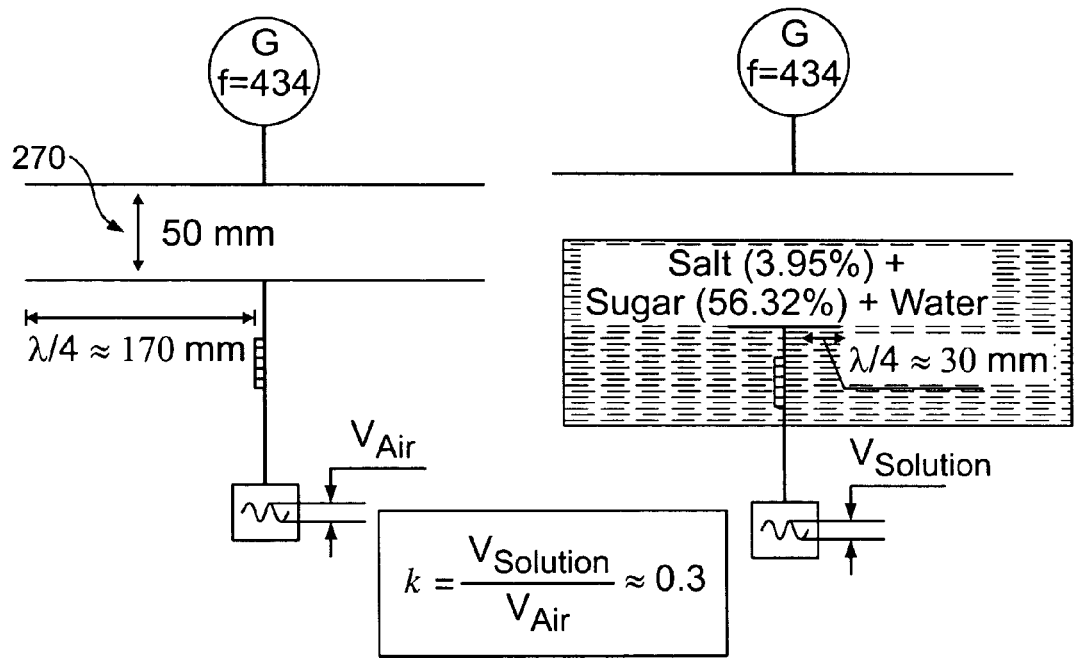
FIG. 16 illustrates a system with a dipole antenna in a simulation medium.
Figure 17:
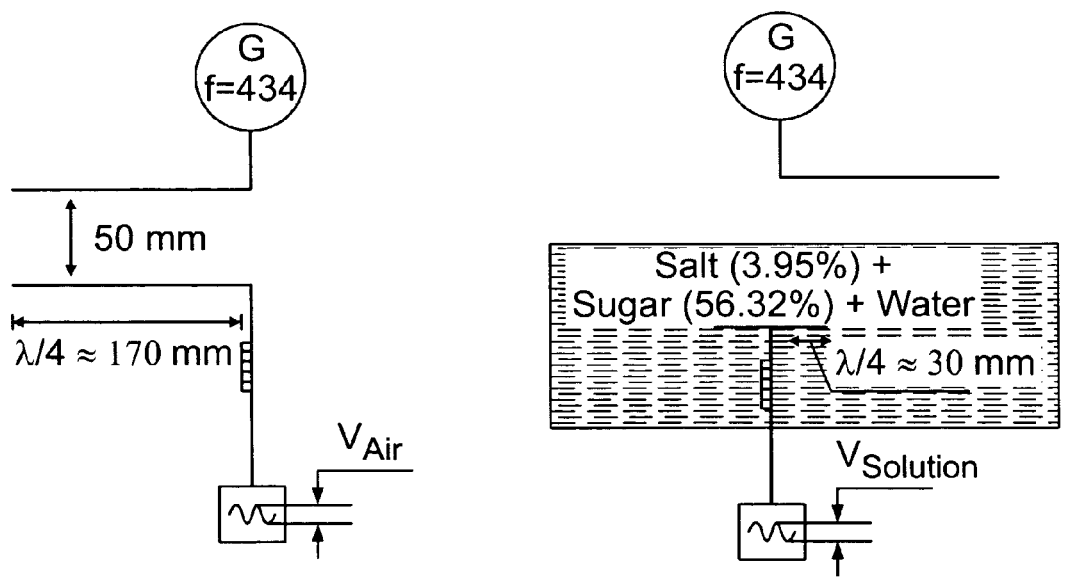
FIG. 17 illustrates a flagpole type antenna in a simulation medium.
Figure 18A:
FIG. 18A is a photograph of a SAW sensor of the resonator type and FIG. 18B for an HF filter type.
Figure 18B:
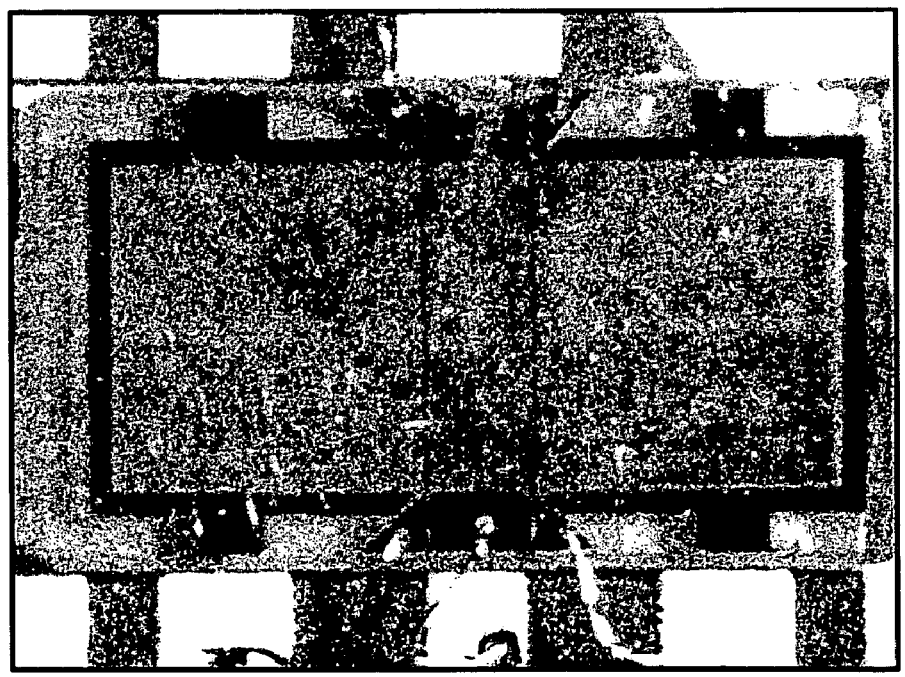

One can see that reduction of the telemetry system efficiency takes place mainly as a result of negative effect of the protecting dielectric coating. If its parameters are optimized, a significant improving of the antenna characteristics can be achieved. In these experiments operation of the antennas 230, 245, optimized for an air medium were investigated. It is much easier to optimize dipole antennas for media with various value of dielectric permittivity. That is why investigations on efficiency of dipole type antenna (FIG. 16) and "flag pole" type antenna (FIG. 17) within the medium, simulating the brain tissue properties, were carried out. An antenna 270 of ~170 mm length is placed in the air, which corresponds to ¼ of wavelength. Within a simulating medium the wavelength reduces by more than 5 times and correspondingly the antenna length is equal to 30 mm. The antenna 270, placed into the simulating medium, was enveloped by thin polyethylene film to avoid direct contact with conducting medium. Distance between the antennae is ~50 cm, and thickness of the simulating liquid layer is several cm. The signal amplitude reduction, caused by insertion of the liquid layer, is no more than ~3 times. This is accurate under the condition that the antennas were optimized for using them in the air and in the solution correspondingly.

In view of the previous discussions and investigations, technical characteristics of the overall most preferred SAW temperature sensor 10 components are tabulated below in Table 9.

In the table below dimensions of the SAW sensors 10 which can be used as temperature sensors are shown:

| sensor | working frequency | dimensions |
| --- | --- | --- |
| ANL (resonator type) | 245 MHz | Ø = 1 cm, h = 0.5 cm |
| "Etalon" (filter) | 172 MHz | 9 × 7 × 2 mm |
| "Etalon" (filter) | 434 MHz | 9 × 7 × 2 mm |
| "Etalon" (delay line) | 434 MHz | 14 × 8 × 2.5 mm |

EXAMPLE 2

Figure 20:
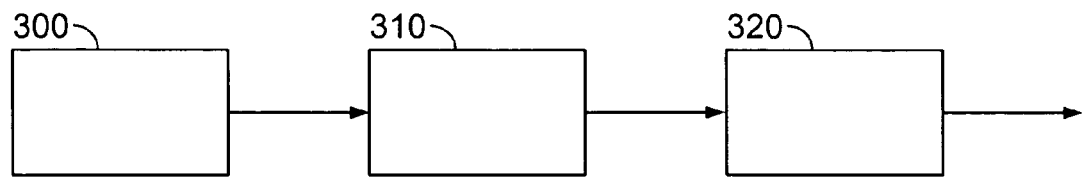
FIG. 20 illustrates a high frequency oscillator block diagram with a frequency modulation of 434 MHz with item 1 a saw tooth generator, item 2 an HF oscillator and item 3 an HF amplifier.

An HF oscillator with FM produces sinusoidal voltage in the frequency range 300 to 900 MHz. HFO block scheme is presented in FIG. 20.

A saw-tooth voltage generator 300 generates a keying signal of saw-tooth shape, necessary for variation of current through transistors of an HF oscillator 310. In this case parameters of their conductivity and diffusion capacities change, it allows to vary the oscillator frequency in the range 300 to 900 MHz. HF amplifier 320 amplifies the HF oscillator signal up to the required level (voltage amplification factor is ~20 dB. We used the purchased device and the scheme, developed in BIOFIL, as a saw-tooth voltage generator 300. A

TABLE 9

|  | SAW device | | | |
| --- | --- | --- | --- | --- |
|  | resonator | filter172 MHz | Filter at 434 MHz | Delay line |
| Resonance frequency, MHz | 245 | 172 | 434 | 434 |
| Phase sensitivity, Phase degree of arc/° C. | 9.4 | 3.0 |  | 144 |
| Delay period | <20 ns | 0.25 µs |  | 10.4 µs |
| Frequency modulation range, MHz |  | 172...177 |  | 420...440 |
| Frequency modulation frequency, kHz |  | 1 |  | 0.66 |
| Intermediate frequency (IF), kHz |  | ≈1 |  | ≈170 |
| Temperature dependence of phase difference at IF |  | linear |  |  |
| Depletion at work within simulation liquid*⁾ |  |  |  | ≈30 |
| Depletion at work within simulation liquid**⁾ |  |  |  | ≈3 |

*⁾antennas are optimized to operate in the air
**⁾antennas are optimized to operate within simulating medium All elements of the SAW sensor 10 have been achieved in order to carry out the monitoring of temperature conditions of a given patient. The technical characteristics show that the accepted concept, choice of circuit design and sensors perform as needed to achieve the desired advantageous results for an afflicted patient.

The following non-limiting Examples illustrate various additional features and advantages of the invention.

EXAMPLE 1

Figure 19A:
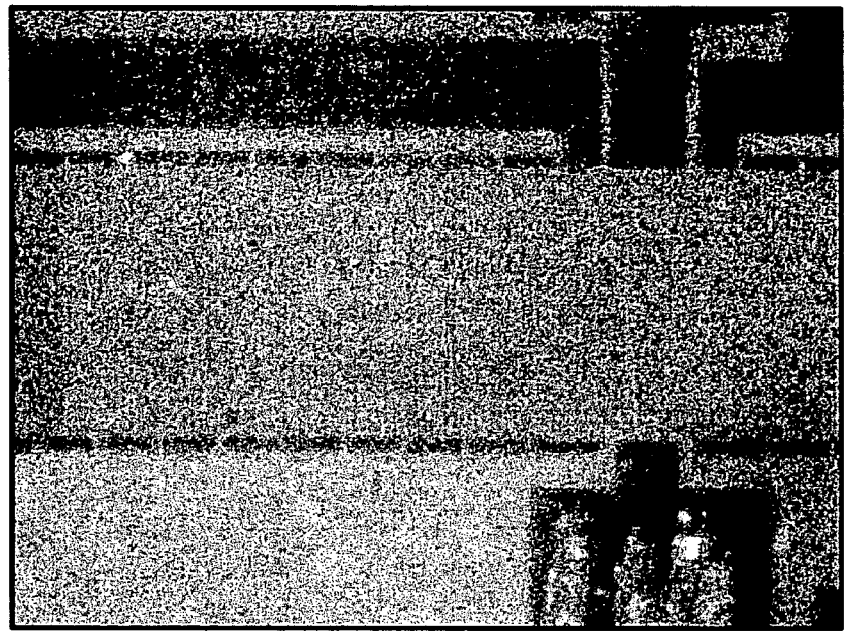
FIG. 19A is a photograph of SAW sensor electrodes of the resonator type SAW sensor (in FIG. 18A)
Figure 19B:
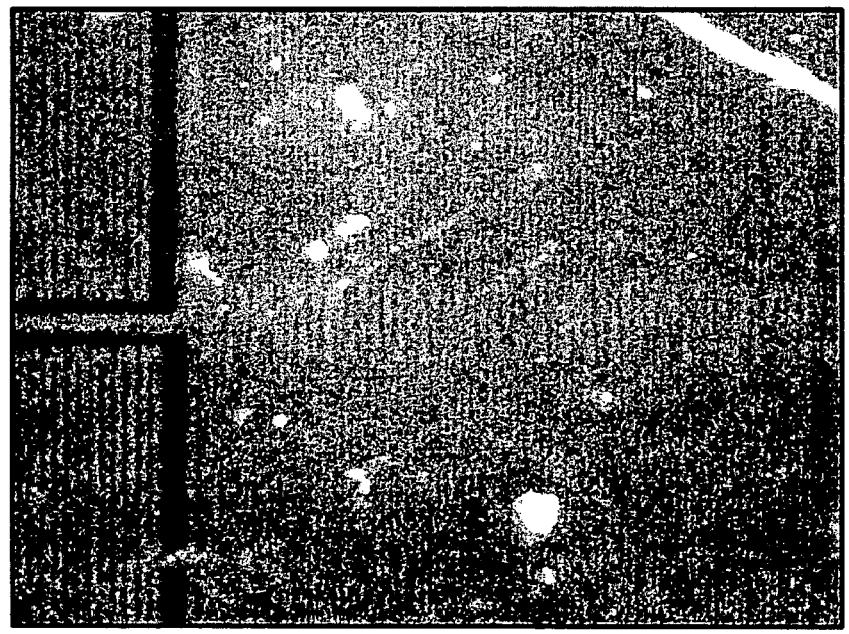
FIG. 19B is for an HF filter type SAW sensor.

The SAW sensor is a crystal substrate with electrodes of comb shape, evaporated on it. FIGS. 19A and 19B present photos of two example sensors 10, which can be used as a sensors in temperature measurement devices.

K174PS4 chip was used as a non-linear element (mixer) for operation frequency 434 MHz.

Figure 22:
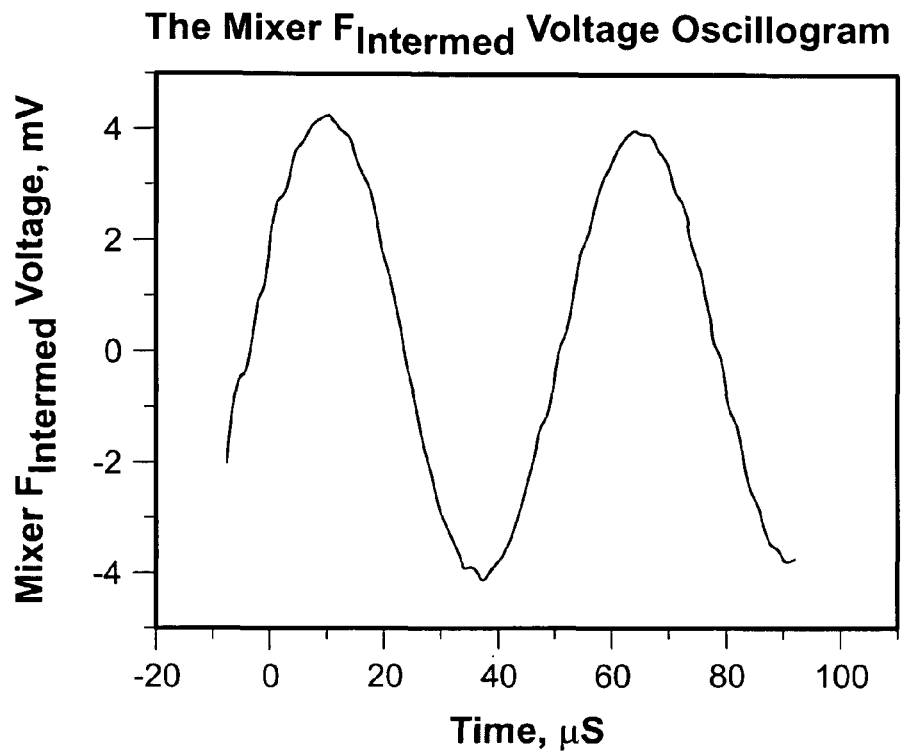
FIG. 22 illustrates behavior of the oscillogram of the mixer output ($F_{intermed}$)

Two signals are sent into the mixer inputs. They are: signal with HFO frequency 556 MHz and heterodyne oscillator signal with frequency 526.8 MHz. At the differential amplifier output we get the signal of intermediate frequency $F_{intermed.}$=18.18 kHz, which oscillogram is presented in FIG. 22.

EXAMPLE 3

Technical characteristics of the preferred SAW temperature sensor 10 components are tabulated below in Table 10.

TABLE

|  | SAW device | | | |
|---|---|---|---|---|
|  | resonator | filter 172 MHz | Filter at 434 MHz | Delay line |
| Resonance frequency, MHz | 245 | 172 | 434 | 434 |
| Phase sensitivity, Phase degree of arc/° C. | 9.4 | 3.0 |  | 144 |
| Delay period | <20 ns | 0.25 μs |  | 10.4 μs |
| Frequency modulation range, MHz |  | 172 ... 177 |  | 420 ... 440 |
| Frequency modulation frequency, kHz |  | 1 |  | 0.66 |
| Intermediate frequency (IF), kHz |  | ≈1 |  | ≈170 |
| Temperature dependence of phase difference at IF |  | linear |  |  |
| Depletion at work within simulation liquid*⁾ |  |  |  | ≈30 |
| Depletion at work within simulation liquid**⁾ |  |  |  | ≈3 |

*⁾antennas are optimized to operate in the air
**⁾antennas are optimized to operate within simulating The presented technical documentation demonstrates that in the project course all elements of the SAW remote temperature sensor have been well worked out unit by unit. The performed technical characteristics show that the accepted concept, choice of circuit design and sensors perform as needed.

Application of delay line at 434 MHz, fabricated in "Etalon" pilot plant, Omsk, Russia, as a SAW sensor seems the most efficient.

EXAMPLE 4

The following devices were used as a temperature sensors:
thermocouple measurement device with absolute measurement error≈3° C., relative measurement error≈0.3° C.
mercury thermometer with relative measurement error≈0.05° C.
temperature sensor, fabricated in BIOFIL on the base of diode. Absolute measurement error≈0.05° C., relative measurement error≈0.005° C.

Thermocouple measurement device and mercurial thermometer are purchased devices. Diode sensor is quite accurate and compact device in contrast to mercurial thermometer. That is why let us focus our attention on its construction, testing and efficiency in more details.

Figure 21:
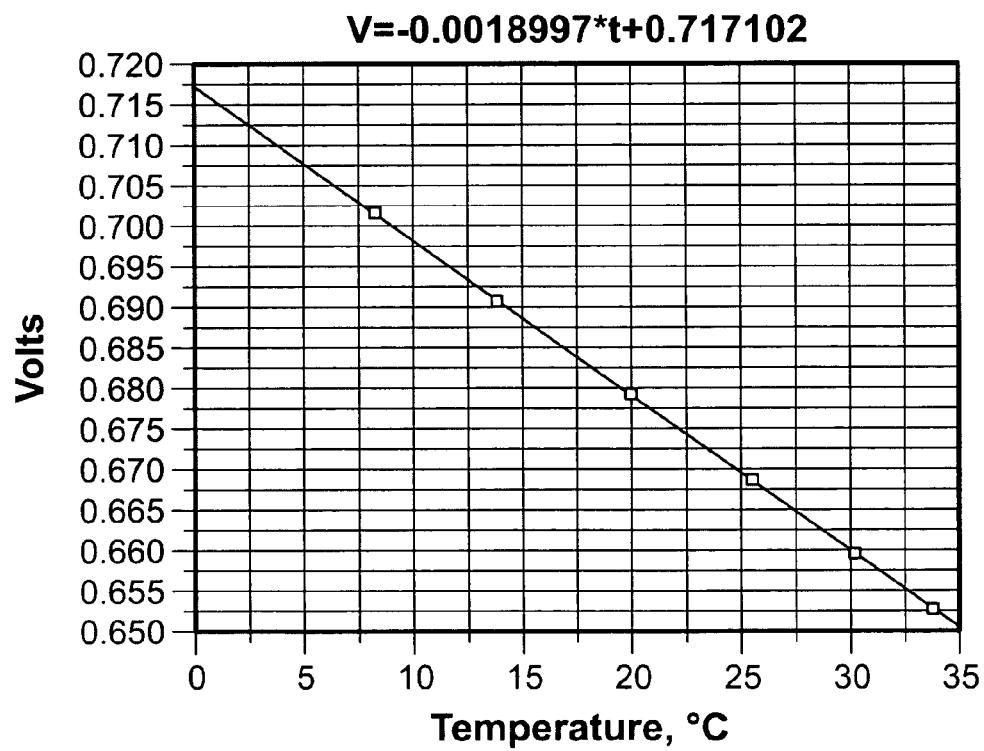
FIG. 21 illustrates calibration results for diode sensor that was used to calibrate the SAW sensor.

The temperature measurement sensor was made on the base of semiconductor diode. It is well known that at passing continuous current through p-n transition, the p-n transition voltage drop depends on p-n transition temperature. We measured voltage drop at forward biased p-n transition at 1 mA continuous current passing. The temperature measurement sensors were calibrated with the help of mercurial thermometer with scale interval 0.1° C., which determines temperature measurement error. The calibration results are presented in FIG. 21.

Ways of Temperature Stabilization and Variation

To stabilize temperature of the object (SAW-sensor) and its specified variation several ways were used:
to provide significant temperature difference between two SAW-sensors.
One sensor was placed into foam plastic cavity. Above it a metal vessel (cooler), containing water-ice mixture in proportion1:1, was located. All assembly was thermally insulated by foam rubber. In the process of the experiment water in the vessel was intermixed periodically. Temperature control in the cooler was carried out by mercurial thermometer.

The second SAW sensor temperature was varied following to similar scheme. The sensor was placed into foam plastic cavity. Above it a metal vessel containing water, previously heated up to 55° C., was located. At time interval, equal to 20 minutes, the water was cooled down to 45° C. and since this moment the signal phase difference measurements started. Temperature control in the second SAW sensor also was carried out by mercurial thermometer.
to provide small temperature difference.

The SAW sensor is placed into the previously cooled glass thermos. Temperature of the SAW element body was measured by mercurial thermometer. Initial temperature inside the thermos is ~0° C. At this temperature the SAW element stays for about 1 hour. Then the thermos temperature starts to rise at the expense of natural heat exchange with ambient environment. The temperature rise velocity is ~15 min/° C. The similar technique allows to carry out measurements at temperature variation 0.5° C. at temperature range 2-7° C.
to provide temperature difference with low accuracy requirements.

Temperature of the SAW sensor body was measured by thermocouple temperature measuring device or diode measuring device, specially fabricated in BIOFIL. The SAW sensor body was heated up to the specified temperature by fan heater. The measurements were conducted at temperature range≈20÷50° C.

EXAMPLE 5

Media, Simulating the Human Body Tissues

To develop telemetry system with implanted sensor one should know electric properties of the medium, into which antenna will be placed. One should know velocity of electric wave propagation in material (u), wavelength (λ), wave penetration depth (δ) and medium internal impedance (η). These characteristics are determined by radio wave frequency(ω) and the medium dielectric properties: dielectric permittivity (∈), magnetic conductivity(μ) and conductivity(σ). The ∈ and μ values of biological tissues are more than 1. That's why the radiation phase velocity and wave length within tissue is less than in the air. In the tissues with high water content the electromagnetic wave length reduces by a factor of 6.5-8.5 comparing with the air. In the tissues with low water content the wavelength reduces only by a factor of 2-2.5. So at the electromagnetic radiation frequency higher than $3 \cdot 10^8$ Hz, the electromagnetic radiation wave length is less than the human body sizes, it determines a local nature of the SHF electromagnetic radiation influence on the human organism. The EMR wavelength values for a number of tissues are presented in Table 11.

TABLE 11

SHF radiation wave length (in cm) within tissues for a set of frequencies[3]

| Tissue | frequency, MHz | | | | | | | |
|---|---|---|---|---|---|---|---|---|
| | 100 | 200 | 400 | 1000 | 3000 | 10000 | 24000 | 35 000 |
| marrow | 116.1 | 62.2 | 32.19 | 12.6 | 3.8 | 1.25 | 0.368 | 0.388 |
| brain | 31.7 | 19.4 | 11.16 | 4.97 | 1.74 | 0.595 | 0.200 | 0.201 |
| fat | 96.0 | 57.1 | 30.90 | 12.42 | 3.79 | 1.450 | 0.680 | — |
| muscle | 27.6 | 16.3 | 9.41 | 4.09 | — | 0.616 | — | — |
| whole blood | 25.1 | 15.3 | 8.89 | 3.87 | 1.36 | 0.449 | 0.214 | 0.167 |
| skin | 28.1 | 17.9 | 10.12 | 4.41 | 1.49 | 0.506 | 0.250 | — |

Figure 23A:
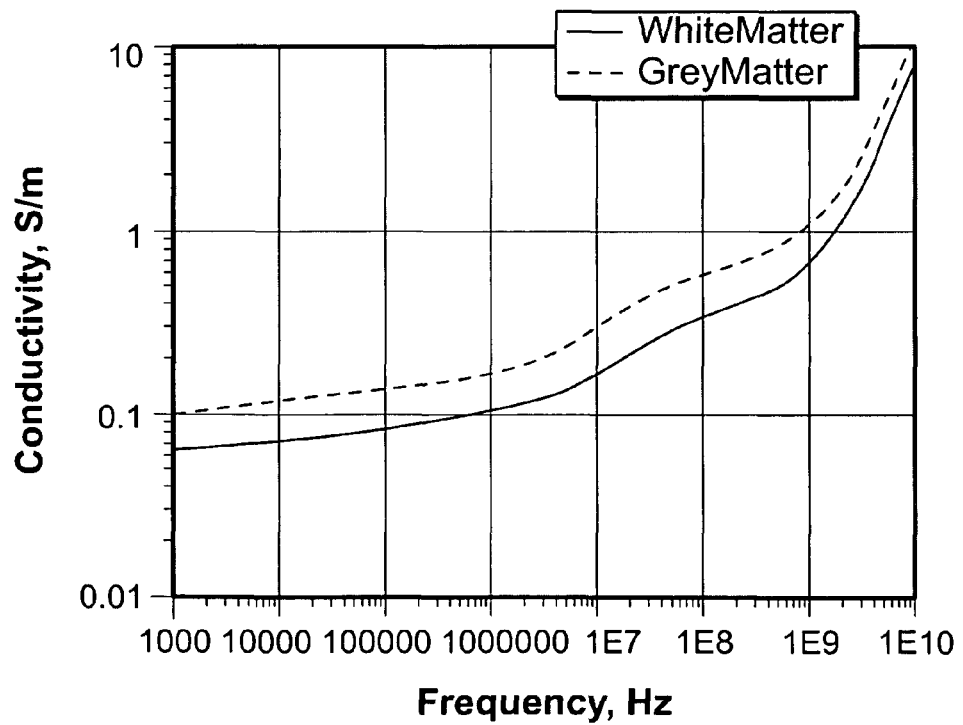
FIG. 23A illustrates conductance as a function of frequency of grey and white brain substance.
Figure 23B:
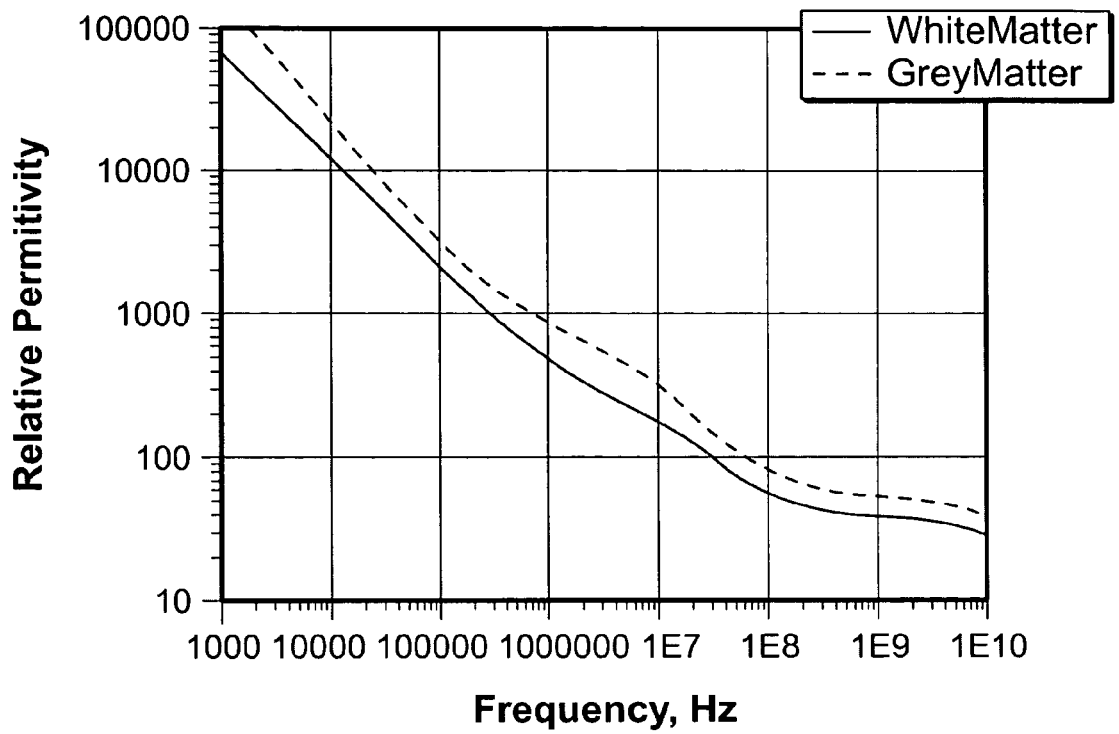
FIG. 23B illustrates permittivity or penetration for grey or white brain substance as a function of frequency.
Figure 23C:
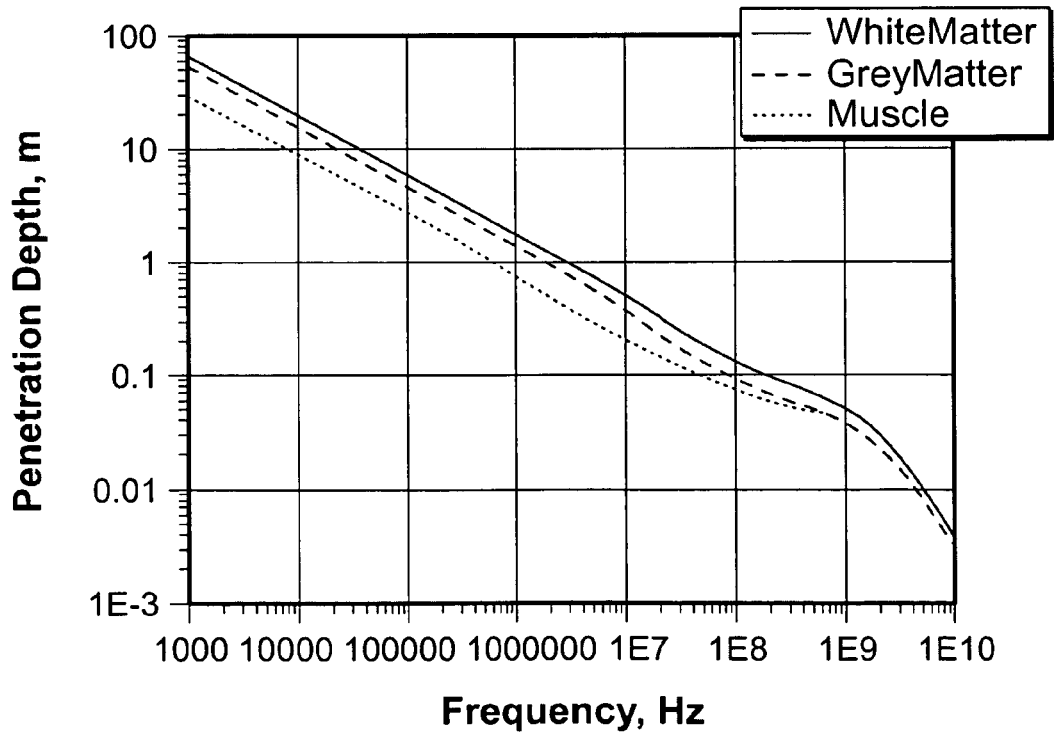
FIG. 23C illustrates electromagnetic radiation penetration depth as a function of frequency for grey and white brain substance and muscle tissue.

Frequency dependences of the most important electric parameters of the medium (conductivity, permittivity and EMR penetration depth) for grey and white matter of the brain plus muscle tissue are presented in FIGS. 23A-23C, respectively.

EXAMPLE 6

The table below presents properties of the devices, used by BIOFIL on various ges of working out and testing the SAW temperature sensors 10.

TABLE

| | | |
|---|---|---|
| 1 | Sinusoid signal generator: | |
| | Frequency variation range, Hz | from 10 kHz to 2 GHz |
| | Signal amplitude, V | 10 mV ÷ 5 V |
| | Frequency resolution | <1 kHz |
| 2 | Oscilloscope Tektronix TDS 3054 | |
| | Bandwidth | 500 MHz |
| | Number of channels | 4 |
| | Maximal record size | 10 000 points |
| | Oscilloscope Tektronix | |

TABLE-continued

| | | |
|---|---|---|
| | TDS 5104 | |
| | Bandwidth, MHz | 1000 MHz |
| | Number of channels | 4 |
| | Maximal record size | 2 000 000 points |
| 3 | Temperature sensor thermocouple | Relative measurements ±0.3° C. Absolute measurements ±3° C. |
| 4 | Temperature sensor diode (fabricated by BIOFIL) | absolute measurements ±0.05° C. relative measurements ±0.005° C. |
| 5 | Fan heater | power 1.2 kW |
| | Temperature variation range | 25 ÷ 45° C. |
| 6 | Thermal electric battery | TЭMO-7 (Peltie element) |
| | Temperature variation range | 25 ÷ 47° C. |
| 7 | high frequency modulator (fabricated by BIOFIL) | Modulation frequency ≈100 kHz Pulse duration ≈200 ns |

EXAMPLE 7

SAW Sensor Test Data

The following parameters were measured experimentally:

| | f MHz | $t_{DL}$ μs | K | τ μs | $S_T^{\Delta\phi}$ angle degrees/° C. | δT ° C. |
|---|---|---|---|---|---|---|
| ANL | 245.2 ± 0.1 | <0.02 | 0.1 | <0.005 | 9.4 ± 0.9 | ±0.02 |
| BIOFIL | 172.2 ± 0.1 | 0.25 ± 0.025 | 0.3 | 0.1 ± 0.01 | 3.0 ± 0.2 | ±0.07 |
| BIOFIL | 434 ± 0.1 | ~0.1 | 0.7 | — | ~1.5 | 0.14 |
| BIOFIL | 434 ± 0.1 | 10.2 ± 0.2 | 0.03 | — | 144 ± 5 | ±0.0015 | f - resonance frequency
$t_{DL}$ - delay time
τ - pulse rise time
K = $U_{in}/U_{out}$ @ f
$S_T^{\Delta\phi}$ - temperature sensitivity
δT = $\Delta\phi_{min}/S_T^{\Delta\phi}$ - temperature resolution It should be understood that various changes and modifications referred to in the embodiment described herein would be apparent to those skilled in the art. Such changes and modifications can be made without departing from the spirit and scope of the present invention.

What is claimed is:

1. A system for predicting or detecting a seizure in a patient, comprising:
a surface acoustic wave probe configured to output a surface acoustic wave and configured to detect a change in temperature of the brain of the patient, the surface acoustic wave probe is implantable in the patient and includes:
a substrate characterized by at least one propagation property of the surface acoustic wave, the at least one propagation property being variable as a function of the substrate temperature;
a first transducer located on the substrate, the first transducer adapted to output the surface acoustic wave in response to an interrogation RF signal; and
a second transducer responsive to the surface acoustic wave propagating the substrate and adapted to output an electric field in response thereto, the second transducer located on the substrate and separated from the first transducer by a distance;

a first RF antenna coupled to the first transducer, the first RF antenna configured to receive the interrogation RF signal;

a second RF antenna coupled to the second transducer, the second RF antenna configured to transmit an output RF signal in response to the electric field, the output RF signal altered in relation to the interrogation RF signal by the at least one propagation property such that the output RF signal is indicative of the temperature of the brain of the patient proximate the substrate; and an interrogation/control unit disposed external to the patient, the interrogation/control unit configured to activate the surface acoustic wave probe, and to receive the RF output signal to detect or predict a seizure in the patient based on a detected change in the temperature of the brain of the patient.

2. The system as defined in claim 1 wherein the surface acoustic wave probe includes a delay line configuration that includes the first RF antenna and the second RF antenna.

3. The system as defined in claim 1 further comprising a reference surface acoustic wave probe maintained at a substantially constant temperature, the reference surface acoustic wave probe configured to receive the interrogation RF signal and output a reference signal to the interrogation/control unit to provide a differential reference in relation to the output RF signal for determining the change in temperature of the brain of the patient.

4. The system as defined in claim 3 wherein the surface acoustic waves introduce phase change between the interrogation RF signal and the output RF signal and delay time parameters sensitive to the change in temperature of the brain of the patient, and wherein the change in temperature of the brain is determined from one or more of the phase change and the delay time of the output RF signal in relation to the interrogation RF signal.

5. The system as defined in claim 3 wherein the surface acoustic waves include a parameter of carrier frequency phase change characteristic of temperature change in the brain of the patient.

6. The system as defined in claim 1 further including a cooling unit disposed in the brain of the patient, the cooling unit able to reduce the temperature of the brain of the patient.

7. The system as defined in claim 6 wherein in response to the output RF signal, the interrogation/control unit operatively controls the cooling unit responsive to the RF interrogation signal.

8. The system as defined in claim 1 wherein the first transducer comprises a first interdigital transducer and the second transducer comprises a second interdigital transducer.

9. The system as defined in claim 8 wherein the first transducer is a measurement sensor disposed in an epileptogenic region and the second transducer is a reference sensor disposed in a non-epileptogenic region selected from inside the brain and outside the brain.

10. The system as defined in claim 1 wherein the first RF antenna and the second RF antenna each comprise a zig-zag antenna with an input resistance of about 50 ohms.

11. The system as defined in claim 1 wherein the surface acoustic wave probe comprises a symmetric surface acoustic wave filter.

12. The system as defined in claim 1 wherein at least one of the first and the second RF antenna is covered with a dielectric coating and the at least first and the second RF antenna design modified to optimize efficiency while implanted with the dielectric coating.

13. The system as defined in claim 1 wherein the interrogation/control unit is further configured to analyze the RF output signal to determine whether a seizure is imminent for the patient based on the detected change in temperature.

14. The system as defined in claim 13 further comprising a cooling unit implantable in the patient in relation to a seizure-prone area of the brain, the cooling unit automatically triggerable by the interrogation/control unit upon detection of an imminent seizure.

15. The system as defined in claim 3 wherein the system is defined by a sensitivity of up to about 1.4 millikelvin.

\* \* \* \* \*